US012788652B2

(12) United States Patent
Sukumaran et al.

(10) Patent No.: US 12,788,652 B2
(45) Date of Patent: Nov. 10, 2026

(54) PATIENT SUPPORT APPARATUS WITH AUTOMATIC SCALE FUNCTIONALITY

(71) Applicant: Stryker Corporation, Kalamazoo, MI (US)

(72) Inventors: Sujay Sukumaran, Portage, MI (US); Madhu Thomas, London (CA); Seyed Behrad Ghodsi, Portland, OR (US); Tracy Leanne Fried, Sarasota, FL (US); Michael Joseph Hayes, Kalamazoo, MI (US); Berkay Güncan, Talas (TR); Christian Fulljames, Grand Rapids, MI (US); Curt Stienstra, Lowell, MI (US); Daniel Dehoog, Grand Rapids, MI (US)

(73) Assignee: Stryker Corporaton, Portage, MI (US)

( * ) Notice: Subject to any disclaimer, the term of this patent is extended or adjusted under 35 U.S.C. 154(b) by 311 days.

(21) Appl. No.: 18/573,129

(22) PCT Filed: Oct. 7, 2022

(86) PCT No.: PCT/US2022/046078
§ 371 (c)(1),
(2) Date: Dec. 21, 2023

(87) PCT Pub. No.: WO2023/064182
PCT Pub. Date: Apr. 20, 2023

(65) Prior Publication Data

US 2024/0299226 A1 Sep. 12, 2024

Related U.S. Application Data

(60) Provisional application No. 63/342,899, filed on May 17, 2022, provisional application No. 63/255,211, filed on Oct. 13, 2021.

(51) Int. Cl.
*A61G 7/05* (2006.01)
*A61B 5/00* (2006.01)
(Continued)

(52) U.S. Cl.
CPC .......... *A61G 7/0527* (2016.11); *A61B 5/1115* (2013.01); *A61B 5/7435* (2013.01); *A61B 90/361* (2016.02)

(58) Field of Classification Search
CPC ............................ A61B 5/6892; A61B 5/1115
(Continued)

(56) References Cited

U.S. PATENT DOCUMENTS 8,413,271 B2 * 4/2013 Blanchard .............. A61G 7/001
5/173
8,752,220 B2 * 6/2014 Soderberg ............ A61G 7/0524
5/426
(Continued)

FOREIGN PATENT DOCUMENTS

WO 2023278478 1/2023
WO WO-2023063182 A1 * 4/2023 ............ C08F 220/04

OTHER PUBLICATIONS

International Search Report and Written Opinion, PCT/US2022/046078. dated Feb. 24, 2023, 20 pages.

*Primary Examiner* — John E Breene
(74) *Attorney, Agent, or Firm* — Gardner, Linn, Burkhart & Ondersma LLP

(57) ABSTRACT

A patient support apparatus, such as a bed, cot, stretcher, etc., includes a scale system adapted to automatically detect when an object is added to a support surface of the patient support apparatus. An onboard controller is configured to take one or more actions in response to the detection of the added object. Such actions include, but are not limited to, sending a message wirelessly to the object, capturing an
(Continued)

image of the object with a camera, marking a segment of a video that encompasses the addition of the object, and/or determining if a change in a center of gravity caused by the addition of the object can be completely attributed to the object's addition, or if it is due to other factors, such as patient movement. A display may show a bed icon with an object icon positioned at the same location as the object.

19 Claims, 10 Drawing Sheets

(51) Int. Cl.
*A61B 5/11* (2006.01)
*A61B 90/00* (2016.01)

(58) Field of Classification Search
USPC .......................................................... 177/144
See application file for complete search history.

(56) References Cited

U.S. PATENT DOCUMENTS

| | | | | |
|---|---|---|---|---|
| 9,814,410 | B2 | 11/2017 | Kostic et al. | |
| 10,420,688 | B2 * | 9/2019 | Furman | A61G 7/018 |
| 10,786,408 | B2 * | 9/2020 | Sidhu | A61G 13/06 |
| 10,904,492 | B2 | 1/2021 | Derenne et al. | |
| 11,033,233 | B2 * | 6/2021 | Hayes | A61B 5/746 |
| 11,062,585 | B2 * | 7/2021 | Durlach | A61G 7/0524 |
| 11,410,524 | B2 * | 8/2022 | Durlach | A61B 5/1115 |
| 12,465,290 | B2 * | 11/2025 | Hayes | A61B 5/7435 |
| 2014/0039351 | A1 | 2/2014 | Mix et al. | |
| 2015/0109442 | A1 | 4/2015 | Derenne et al. | |
| 2015/0281659 | A1 | 10/2015 | Hood et al. | |
| 2016/0106345 | A1 | 4/2016 | Kostic et al. | |
| 2016/0213537 | A1 | 7/2016 | Hayes et al. | |
| 2016/0367420 | A1 | 12/2016 | Zerhusen et al. | |
| 2018/0333082 | A1 | 11/2018 | Hoffman et al. | |
| 2019/0231620 | A1 * | 8/2019 | Menkedick | G01G 19/445 |
| 2020/0203010 | A1 | 6/2020 | Durlach | |
| 2021/0298682 | A1 | 9/2021 | Hayes et al. | |
| 2024/0277543 | A1 * | 8/2024 | Sukumaran | A61G 7/005 |

* cited by examiner

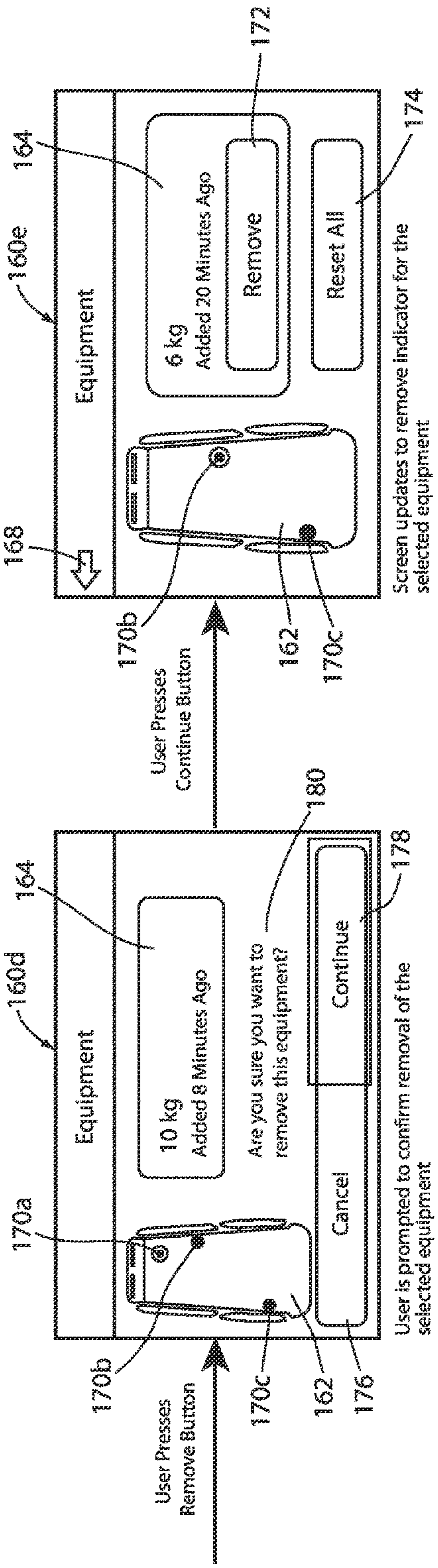
FIG. 12
FIG. 13
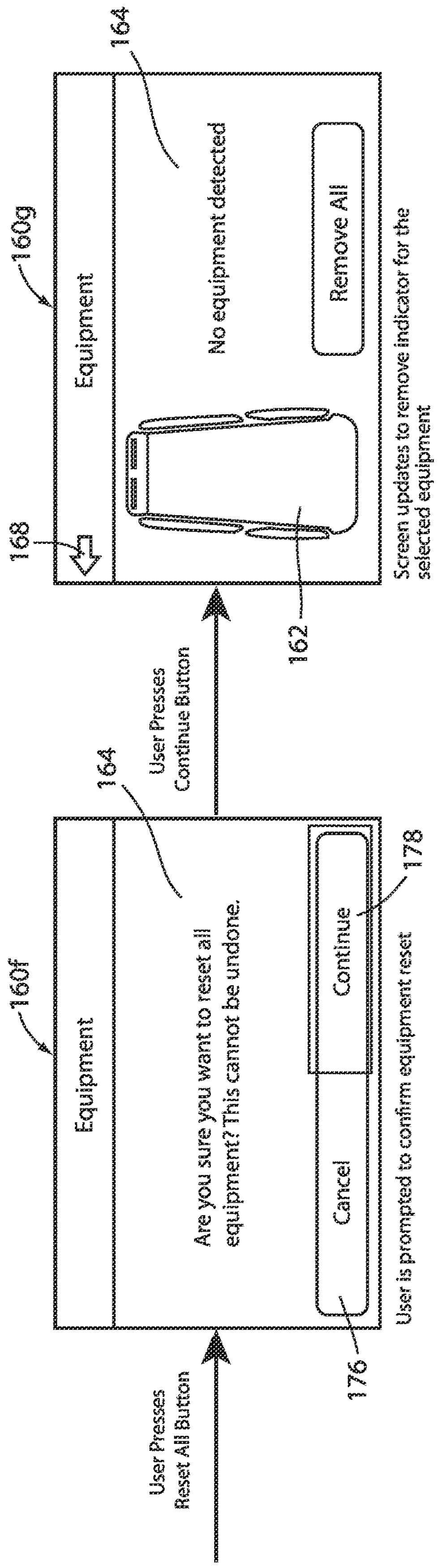
FIG. 14
FIG. 15

PATIENT SUPPORT APPARATUS WITH AUTOMATIC SCALE FUNCTIONALITY

CROSS-REFERENCE TO RELATED APPLICATIONS

This application claims priority to U.S. provisional patent application Ser. No. 63/255,211 filed Oct. 13, 2021, by inventors Sujay Sukumaran et al. and entitled PATIENT SUPPORT APPARATUS WITH AUTOMATIC SCALE FUNCTIONALITY, and to U.S. provisional patent application Ser. No. 63/342,899 filed May 17, 2022, by inventors Sujay Sukumaran et al. and entitled PATIENT SUPPORT APPARATUS WITH AUTOMATIC SCALE FUNCTIONALITY, the complete disclosures of both of which are incorporated herein by reference.

BACKGROUND

The present disclosure relates to patient support apparatuses, such as beds, cots, stretchers, operating tables, recliners, or the like. More specifically, the present disclosure relates to patient support apparatuses that include a scale system.

Existing hospital beds and/or stretchers often include a scale system that is used for weighing the patient. Such scale systems not only measure the weight of the patient, but they also measure the weight of any objects that have been placed on the support surface of the patient support apparatus. In order to generate accurate measurements of the patient's weight, it is therefore necessary to account for the weight of any objects that may have been added to the patient support apparatus.

SUMMARY

According to various aspects of the present disclosure, an improved patient support apparatus is provided that helps caregivers monitor the addition and/or removal of non-patient objects from the patient support apparatus, thereby providing the caregivers with more accurate information regarding the accuracy of any weight reading they take with the scale system. A display on the patient support apparatus provides a number of helpful screens for assisting the caregiver in easily maintaining an accurate log of non-patient items that have been added to and/or removed from the patient support apparatus, thereby giving greater confidence to the caregiver of the accuracy of any patient weight readings that are taken. In some aspects, the addition of an object to, and/or the removal of an object from, the patient support apparatus is automatically detected by the scale system, and one or more actions are automatically undertaken by the patient support apparatus in response thereto. Such automatic actions may include attempting to establish communication with the object, or an electronic tag coupled to the object; capturing an image of the object with a camera; marking a segment of a video that encompasses the addition/removal of the object; and/or determining if a change in a center of gravity caused by the addition of the object can be completely attributed to the object's addition, or if it is due to other factors, such as patient movement. Still other features and functions of the present disclosure will be apparent to a person skilled in the art in light of the following written description and the accompanying drawings.

A patient support apparatus according to a first aspect of the present disclosure includes a support surface, a plurality of force sensors, a transceiver, and a controller. The support surface is adapted to support a patient thereon. The force sensors are adapted to detect downward forces exerted on the support surface. The controller is adapted to analyze outputs from the plurality of force sensors to determine if a load added to the support surface corresponds to a patient or an object. If the load corresponds to an object, the controller is further adapted to send a message wirelessly via the transceiver to the object to attempt to establish communication with the object or an electronic tag coupled to the object.

According to another aspect of the present disclosure, a patient support apparatus is provided that includes a support surface, a plurality of force sensors, a camera, and a controller. The support surface is adapted to support a patient thereon. The force sensors are adapted to detect downward forces exerted on the support surface. The camera includes a field of view aimed to encompass the support surface, and the controller is adapted to analyze outputs from the plurality of force sensors to determine if a load added to the support surface corresponds to a patient or an object. If the load corresponds to an object, the controller is further configured to automatically capture an image of the object using the camera.

According to another aspect of the present disclosure, a patient support apparatus is provided that includes a support surface, a plurality of force sensors, a video camera, and a controller. The support surface is adapted to support a patient thereon. The force sensors are adapted to detect downward forces exerted on the support surface. The video camera includes a field of view aimed to encompass the support surface, and the controller is adapted to analyze outputs from the plurality of force sensors to determine if a load added to the support surface corresponds to a patient or an object. If the load corresponds to an object, the controller is further adapted to mark a segment of video captured by the video camera in response to determining that the load corresponds to an object.

According to still another aspect of the present disclosure, a patient support apparatus is provided that includes a support surface, a plurality of force sensors, and a controller. The support surface is adapted to support a patient thereon. The force sensors are adapted to detect downward forces exerted on the support surface, and the controller is adapted to analyze outputs from the plurality of force sensors to repetitively calculate a center of gravity of a load exerted on the plurality of force sensors. The controller is further configured to detect when an object is added to the support surface, to determine a center of gravity change between a first center of gravity calculation made before the object was added and a second center of gravity calculation made after the object was added, and to determine if the center of gravity change can be accounted for solely by the addition of the object to the support surface. If not, the controller is configured to issue a notification to a user.

According to still other aspects of the present disclosure, if the load corresponds to a patient, the controller may be configured to not send a message via the transceiver.

In some aspects, the controller is adapted to determine if the load added to the support surface corresponds to a patient or an object by comparing a magnitude of the load to a threshold. If the load is greater than the threshold, the controller is configured to conclude that the load corresponds to a patient, and if the load is less than the threshold, the controller is configured to conclude that the load corresponds to an object.

In some aspects, the patient support apparatus further includes a display in communication with the controller, and the controller is further adapted to determine a location of the object (if the load corresponds to an object) and to display the location on the display.

The display, in some aspects, is a touchscreen, and the controller is further adapted to display a patient support apparatus icon and an object icon on the touchscreen. The controller is still further adapted to display additional information about the object in response to a user pressing on the object icon.

In some aspects, the additional information includes at least one of the following: a weight of the object, a time when the object was added to the patient support apparatus, a day when the object was added to the patient support apparatus, a coordinate location of the object, or an identification of the object.

In some aspects, the segment of video includes a first plurality of video images capturing a first moment before the object is added to the support surface, and a second plurality of video images capturing a second moment after the object has been added to the support surface.

The controller, in some aspects, is further adapted to analyze an image of the object captured by the video camera to determine an identity of the object.

In some aspects, the controller is adapted to forward an image of the object captured by the video camera to a server, and the server is adapted to analyze the image of the object in order to determine an identity of the object.

Alternatively, or additionally, the server may be adapted to share the image of the object with at least one mobile electronic device.

The controller, in some aspects, is configured to automatically send a message to the object, or a tag coupled to the object, wherein the message is adapted to prompt the electronic tag to respond to the message. Alternatively, or additionally, the message may be adapted to prompt the object, or electronic tag, to respond with identification information identifying the object and/or the tag.

In some aspects, the controller is adapted to instruct the camera to capture an image of the object after the object has been added to the support surface, and the controller is further adapted to analyze the image in order to determine a first location estimate of the object relative to the patient support apparatus.

The controller may also be adapted to analyze outputs from the force sensors to determine a second location estimate of the object.

According to some aspects, the controller is further adapted to compare the first location estimate of the object to the second location estimate of the object. The controller may further be adapted to issue a notification if the first location estimate differs from the second location estimate by more than a threshold.

In some aspects, the controller is further adapted to calculate a location of the object if the center of gravity change can be accounted for solely by the addition of the object.

The controller, in some aspects, is configured to determine if the center of gravity change can be accounted for solely by the addition of the object to the support surface by performing the following: (1) determining a weight of the object; (2) determining a ratio of the weight of the object to a weight measured prior to the addition of the object to the support surface; (3) using the ratio to determine a theoretical location where the object would have to be placed to account for the center of gravity change; (4) determining if the theoretical location is inside or outside of a boundary; and (5) concluding the center of gravity change can be accounted for solely by the addition of the object if the theoretical location is inside of the boundary.

In some aspects, the boundary corresponds to a perimeter of the support surface.

The controller, in some aspects, is configured to conclude that the center of gravity change cannot be accounted for solely by the addition of the object if the theoretical location is outside of the boundary.

In some aspects, the controller is further adapted to automatically forward the segment of video to a server via the network, and the server is adapted to share the segment of video with at least one mobile electronic device and/or to analyze the segment of video to determine an identity of the object.

In some aspects, the controller is adapted to analyze the segment of video to determine an identity of the object.

The controller, in some aspects, is adapted to calculate a location of the object if the center of gravity change can be accounted for solely by the addition of the object.

The patient support apparatus, in some aspects, include a display, and the notification includes a message displayed on the display requesting that the user remove the object from the support surface and then place the object back on the support surface.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 12 is a fifth example of the weight log screen illustrating a situation where the user has selected the "remove" option for one of the objects in the weight log;

FIG. 13 is a sixth example of the weight log screen illustrating a situation moments after the caregiver has executed the "remove" function of FIG. 12;

FIG. 14 is a seventh example of the weight log screen illustrating a situation where the user has selected the "reset all" option;

FIG. 15 is an eight example of the weight log screen illustrating a situation moments after the caregiver has executed the "reset all" function of FIG. 14;

DETAILED DESCRIPTION

Figure 1:
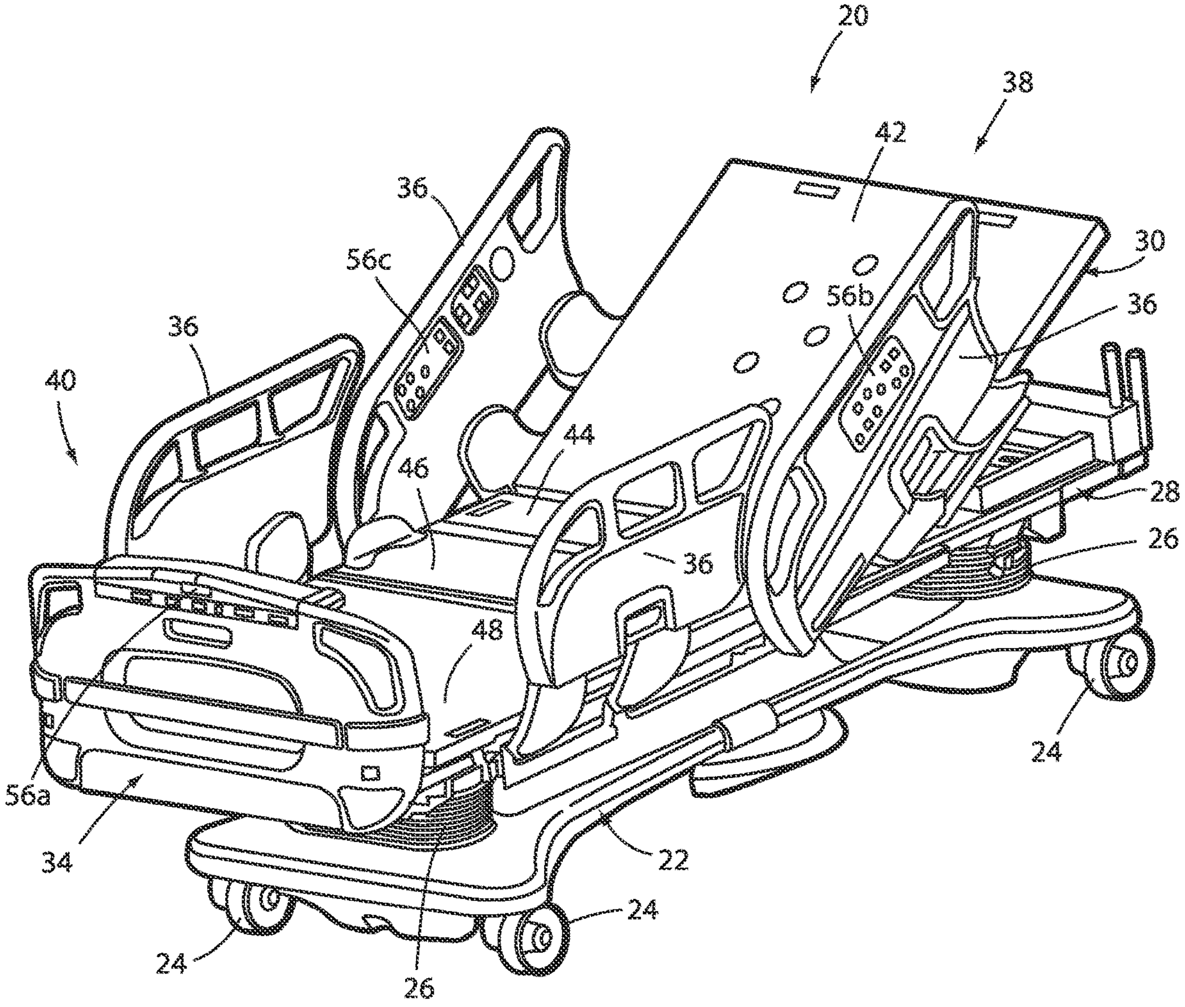
FIG. 1 is a perspective view of a patient support apparatus according to one aspect of the disclosure.

An illustrative patient support apparatus 20 that may incorporate one or more aspects of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, a residential bed, or any other structure capable of supporting a patient, whether stationary or mobile and/or whether medical or residential.

In general, patient support apparatus 20 includes a base 22 having a plurality of wheels 24, a pair of lifts 26 supported on the base, a litter frame 28 supported on the lifts 26, and a support deck 30 supported on the litter frame 28. Patient support apparatus 20 further includes a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36. In some embodiments, siderails 36 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, footboard 34, and siderails 36. Support deck 30 provides a support surface for a mattress (not shown), or other soft cushion, so that a person may lie and/or sit thereon. Support deck 30 is made of a plurality of sections, some of which are pivotable about generally horizontal pivot axes. In the embodiment shown in FIG. 1, support deck 30 includes at least a head section 42, a seat section 44, a thigh section 46, and a foot section 48, all of which generally form flat surfaces for supporting the mattress. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width. Notionally, the first standard width may be considered a 36 inch width, the second intermediate width may be considered a 42 inch width and the third more expanded width may be considered a 48 inch width, although these numerical widths may be varied to comprise different width values.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may be the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with still other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on still other forms different from what is disclosed in the aforementioned references.

Figure 2:
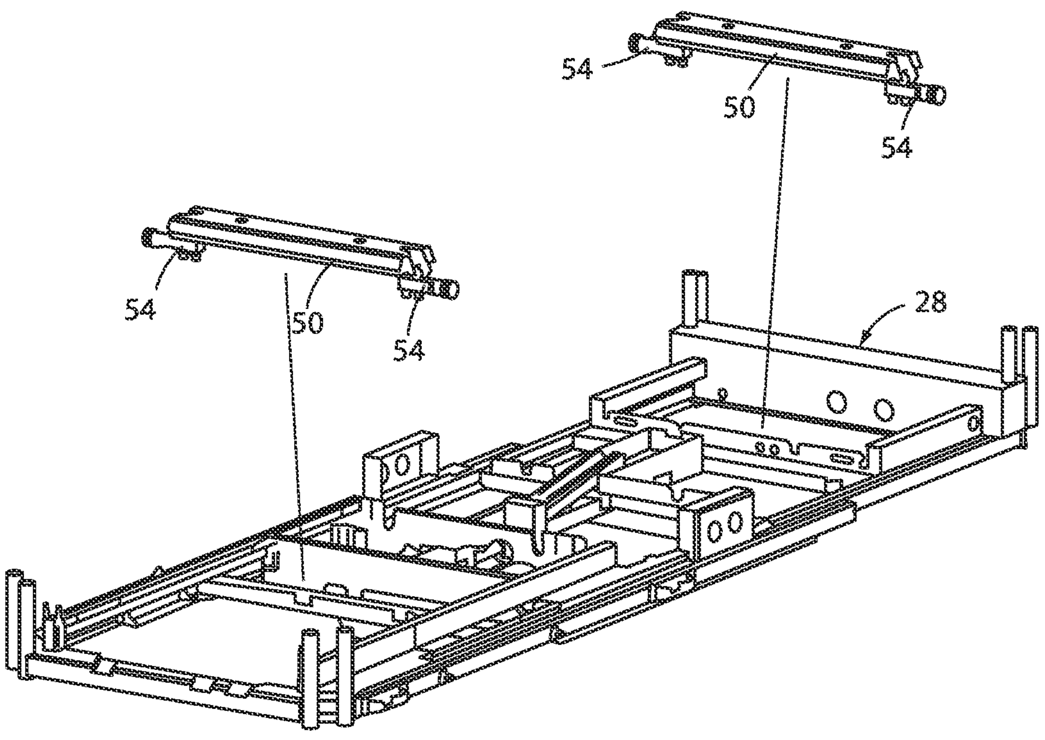
FIG. 2 is a perspective view of a litter frame of the patient support apparatus.
Figure 3:
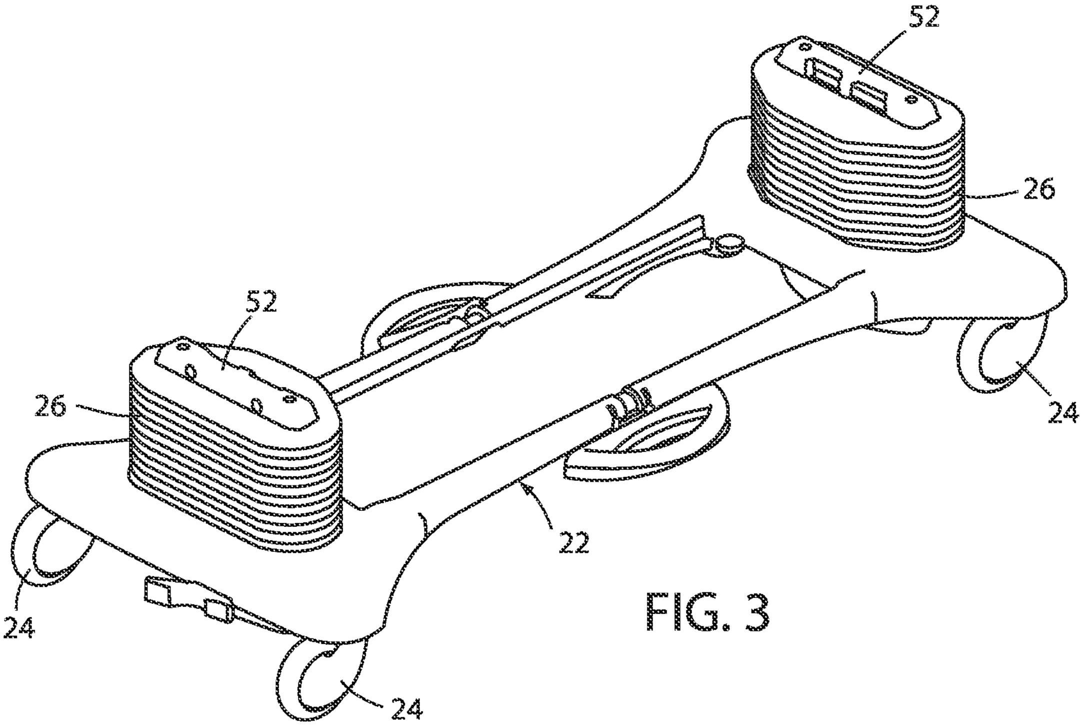
FIG. 3 is a perspective view of a base of the patient support apparatus.
Figure 4:
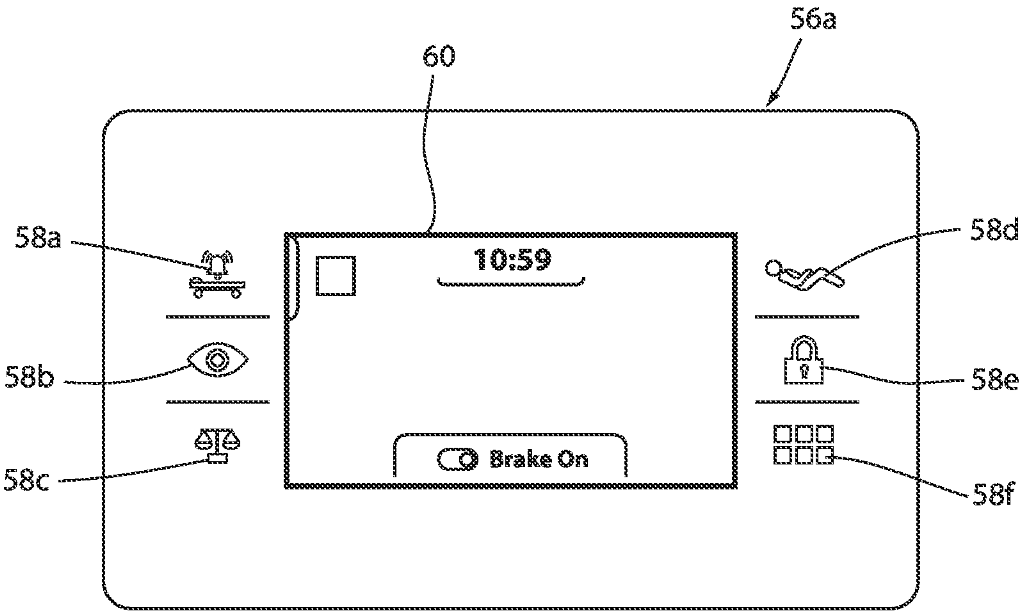
FIG. 4 is a plan view of a control panel that may be included with the patient support apparatus.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of load cells 54. The illustrated embodiment of patient support apparatus 20 therefore includes a total of four load cells 54, although it will be understood by those skilled in the art that different numbers of load cells may be used in accordance with the principles of the present disclosure. Load cells 54 are configured to support litter frame 28. More specifically, load cells 54 are configured such that they provide complete and exclusive mechanical support for litter frame 28 and all of the components that are supported on litter frame 28 (e.g. support deck 30, footboard 34, the headboard, siderails 36, etc.). Because of this construction, load cells 54 are adapted to detect the weight of not only those components of patient support apparatus 20 that are supported by litter frame 28 (including litter frame 28 itself), but also any objects or persons who are wholly or partially being supported by support deck 30. The outputs of load cells 54 are fed into a scale system described in greater detail below Patient support apparatus 20 further includes a plurality of control panels 56 that enable a user of patient support apparatus 20, such as a patient and/or an associated caregiver, to control one or more aspects of patient support apparatus 20. In the embodiment shown in FIG. 1, patient support apparatus 20 includes a footboard control panel **56*a*, a pair of outer siderail control panels 56*b* (only one of which is visible), and a pair of inner siderail control panels 56*c* (only one of which is visible). Footboard control panel 56*a* concealed by a lid in FIG. 1, but is otherwise visible and accessible to a caregiver when the lid is lifted. Footboard control panel 56*a* and outer siderail control panels 56*b* are intended to be used by caregivers, or other authorized personnel, while inner siderail control panels 56*c* are intended to be used by the patient associated with patient support apparatus 20. Each of the control panels 56 includes a plurality of controls 58 (see, e.g. FIGS. 4-5), although each control panel 56** does not necessarily include the same controls and/or functionality.

Among other functions, controls 58 of control panel **56*a* allow a user to control one or more of the following: change a height of support deck 30, raise or lower head section 42, activate and deactivate a brake for wheels 24, arm and disarm one or more patient monitoring functions, change various settings on patient support apparatus 20, view the current location of the patient support apparatus 20 as determined by a location detection system, view what objects-if any-have been added to the patient support apparatus 20 and detected by the scale system, control other aspects of the scale system, and perform still other actions. One or both of the inner siderail control panels 56*c* also include at least one control 58** that enables a patient to call a remotely located nurse (or other caregiver).

Control panel **56*a* includes a display 60 (FIG. 4) configured to display a plurality of different screens thereon. Surrounding display 60 are a plurality of navigation controls 58*a-f* that, when activated, cause the display 60 to display different screens on display 60. For example, when a user presses navigation control 58*a*, control panel 56*a* displays an exit detection control screen on display 60 that includes one or more icons that, when touched, control an onboard exit detection system. The exit detection system is adapted to issue an alert when a patient exits from patient support apparatus 20**. Such an exit detection system may include any of the same features and/or functions as, and/or may be constructed in any of the same manners as, the exit detection systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and/or the exit detection system disclosed in commonly assigned U.S. Pat. No. 5,276,432 issued to Travis and entitled PATIENT EXIT DETECTION MECHANISM FOR HOSPITAL BED, the complete disclosures of both of which are incorporated herein by reference.

When a user presses navigation control **58*b* (FIG. 4), control panel 56*a* displays a patient support apparatus monitoring control screen that includes a plurality of control icons that, when touched, control an onboard monitoring system that monitors one or more components, features, and/or other aspects of patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20 for monitoring parameters of the patient support apparatus 20**.

When a user presses navigation control **58*c*, control panel 56*a* displays a scale control screen that includes a plurality of control icons that, when touched, control the scale system of patient support apparatus 20**. Such a scale system may include any of the same features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system may utilize the same force sensors that are utilized by the exit detection system, in some embodiments, or it may utilize one or more different sensors. Further details regarding the scale system are described in greater detail below.

When a user presses navigation control **58*d*, control panel 56 displays a motion control screen that includes a plurality of control icons that, when touched, control the movement of various components of patient support apparatus 20, such as, but not limited to, the height of litter frame 28 and the pivoting of head section 42. In some embodiments, the motion control screen displayed on display 60 in response to pressing control 58*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20**.

When a user presses navigation control 58*e* (FIG. 4), control panel 56*a* displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosure of which is incorporated herein by reference. Other types of motion lockouts may be included within patient support apparatus 20.

When a user presses on navigation control 58*f*, control panel 56*a* displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, location information, medical device association information, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of menus and/or settings may be included within patient support apparatus 20. In at least one embodiment, utilization of navigation control 58*f* allows a user to navigate to a screen that enables a user to configure the communication settings between patient support apparatus 20 and one or more wall units. Examples of the type of communication settings that may be configured in this manner are disclosed in, and illustrated in FIGS. 9-15 of, commonly assigned U.S. patent application Ser. No. 63/26,937 filed May 19, 2020, by inventors Alexander Bodurka et al. and entitled PATIENT SUPPORT APPARATUSES WITH HEADWALL COMMUNICATION, the complete disclosure of which is incorporated herein by reference.

For all of the navigation controls 58*a-f* (FIG. 4), screens other than the ones specifically mentioned above may be displayed on display 60 in other embodiments of patient support apparatus 20 in response to a user pressing these controls. Thus, it will be understood that the specific screens mentioned above are merely representative of the types of screens that are displayable on display 60 in response to a user pressing on one or more of navigation controls 58*a-f*. It will also be understood that, although navigation controls 58*a-f* have all been illustrated in the accompanying drawings as dedicated controls that are positioned adjacent display 60, any one or more of these controls 58*a-f* could alternatively be touchscreen controls that are displayed at one or more locations on display 60. Still further, although controls 58*a-f* have been shown herein as buttons, it will be understood that any of controls 58*a-f* could also, or alternatively, be switches, dials, or other types of non-button controls.

Figure 5:
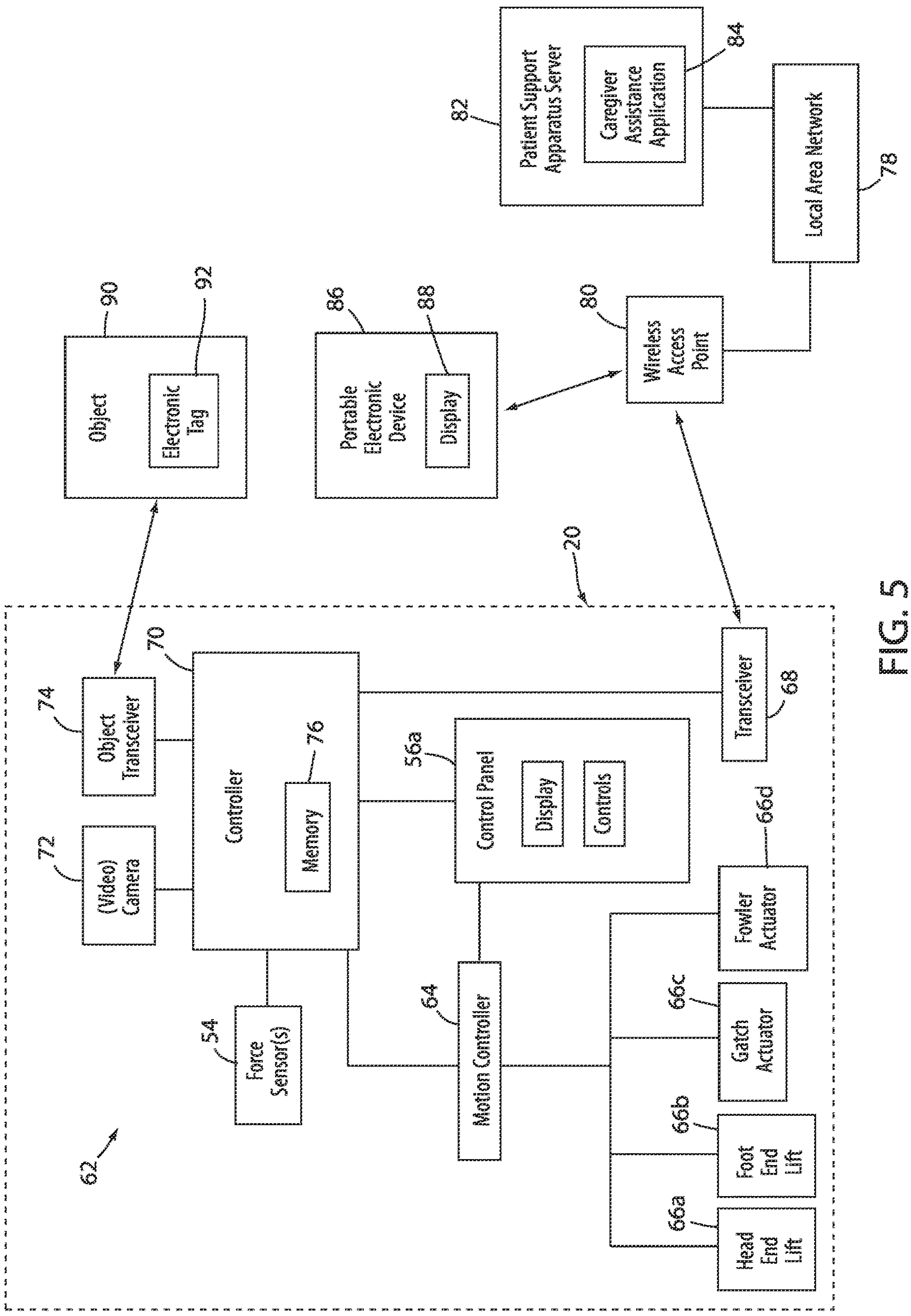
FIG. 5 is a block diagram of a control system of the patient support apparatus, as well as several external devices with which the patient support apparatus may be configured to communicate.

As shown in FIG. 5, patient support apparatus 20 includes a control system 62 that controls various aspects of patient support apparatus 20. Control system 62 includes control panels 56 (only one of which—56*a*—is shown in FIG. 5), a motion controller 64, a plurality of motorized actuators 66, a network transceiver 68, a main controller 70, a camera 72 (which may be a still camera or a video camera), an object transceiver 74, and a plurality of force sensors or load cells 54. Main controller 70 includes a memory 76. Main controller 70 and force sensors 54 together act as both a scale system and an exit detection system. When acting as an exit detection system, main controller 70 and force sensors 54 are adapted to determine when an occupant leaves patient support apparatus, or moves in a way indicative of an imminent departure from the patient support apparatus. In such situations, main controller 70 is configured to issue an alert and/or notification to appropriate personnel so that proper steps can be taken in response to the occupant's departure, or imminent departure, in a timely fashion.

Force sensors 54 are adapted to detect downward forces exerted by an occupant of support deck 30. Thus, when an occupant is positioned on support deck 30 and remains substantially still (i.e. not moving in a manner involving accelerations that cause forces to be exerted against support deck 30), force sensors 54 will detect the weight of the occupant (as well as the weight of any components of patient support apparatus 20 that are supported-directly or indirectly-by force sensors 54). In at least one embodiment, force sensors 54 are load cells. However, it will be understood by those skilled in the art, that force sensors 54 may be implemented as other types of sensors, such as, but not limited to, linear variable displacement transducers and/or any one or more capacitive, inductive, and/or resistive transducers that are configured to produce a changing output in response to changes in the force exerted against them.

Main controller 70 and motion controller 64 are constructed of any electrical component, or group of electrical components, that are capable of carrying out the functions described herein. In many embodiments, controllers 64 and 70 are conventional microcontrollers, although not all such embodiments need include a microcontroller. In general, controllers 64 and 70 include any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. Indeed, in some embodiments, main controller 70 and motion controller 64 are combined with each other and/or with other circuitry or controllers that are present on patient support apparatus 20. The instructions followed by controllers 64 and 70 in carrying out the functions described herein, as well as the data necessary for carrying out these functions, are stored in one or more memories that are accessible to them (e.g. memory 76 for main controller 70).

Although patient support apparatus 20 includes a total of four force sensors 54, it will be understood by those skilled in the art that different numbers of force sensors 54 may be used in accordance with the principles of the present disclosure. Force sensors 54, in at least one embodiment, are configured to support litter frame 28. When so configured, force sensors 54 are constructed to provide complete and exclusive mechanical support for litter frame 28 and all of the components that are supported on litter frame 28 (e.g. deck 30, footboard 34, and, in some embodiments, siderails 36). Because of this construction, force sensors 54 are adapted to detect the weight of not only those components of patient support apparatus 20 that are supported by the litter frame 28 (including litter frame 28 itself), but also any objects or persons who are positioned either wholly or partially on support deck 30. By knowing the weight of the components of the patient support apparatus 20 that are supported on litter frame 28, controller 70 is able to determine a tare weight that, when subtracted from a total weight sensed after a patient is supported on support deck 30, yields a patient weight.

In some embodiments, the physical location of the force sensors 54 on patient support apparatus 20 may be modified to be located on the base frame, such as shown in commonly assigned U.S. patent application Ser. No. 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. In other embodiments, the physical location of the force sensors 54 on patient support apparatus 20 may be the same as the position of the load cells disclosed in commonly assigned U.S. patent application Ser. No. 15/266,575 filed Sep. 15, 2016, by inventors Anuj Sidhu et al. and entitled PERSON SUPPORT APPARATUSES WITH EXIT DETECTION SYSTEMS, the complete disclosure of which is also incorporated herein by reference. In still other embodiments, the physical location of the force sensors 54 may be the same as the position of the load cells disclosed in U.S. Pat. No. 7,962,981 issued to Lemire et al. and entitled HOSPITAL BED, the complete disclosure of which is also incorporated herein by reference. In still other embodiments, force sensors 54 may be positioned on patient support apparatus 20 at still other locations.

Motion controller 64 (FIG. 5) is adapted to control the movement of a plurality of components of patient support apparatus 20. These components includes, but are not limited to, a head end lift actuator 66*a*, a foot end lift actuator 66*b*, a gatch actuator 66*c*, and a Fowler actuator 66*d*. Each of these actuators 66*a-d* may comprise a linear actuator with a motor built therein. In some embodiments, the linear actuator may be of the type disclosed in commonly assigned U.S. patent application Ser. No. 15/449,277 filed Mar. 3, 2017, by inventors Anish Paul et al. and entitled PATIENT SUPPORT APPARATUS WITH ACTUATOR FEEDBACK, the complete disclosure of which is incorporated herein by reference. In other embodiments, other types of powered actuators may be used, such as, but not limited to, hydraulic and/or pneumatic actuators.

In some embodiments, motion controller 64 operates in the same or similar manners to the main microcontroller 58 and its associated circuitry disclosed in commonly assigned U.S. Pat. No. 10,420,687 issued Sep. 24, 2019, to inventors Aaron Furman et al. and entitled BATTERY MANAGEMENT FOR PATIENT SUPPORT APPARATUSES, the complete disclosure of which is incorporated herein by reference. In such embodiments, motion controller 64 controls the sending of pulse width modulated (PWM) signals to the motors contained within actuators 66*a-d*, thereby controlling both the speed and the direction of movement of these actuators. Motion controller 64 may take on other forms as well.

Motion controller 64 is in communication with control panel 56 and receives signals from control panel 56 indicating when a user wishes to move one or more components of patient support apparatus 20. That is, control panel 56 includes one or more controls 58 that are adapted, when activated, to instruct motion controller 64 to carry out the desired movement of the various movable components of patient support apparatus 20, as well as one or more controls for stopping such motion. Such movement includes, but is not limited to, raising and lowering the height of litter frame 28, pivoting the Fowler section 42 up and down about a generally horizontal axis (extending laterally from one side of the patient support apparatus 20 to the other), and/or lifting and lowering a knee gatch on patient support apparatus 20.

Head end lift actuator 66*a* is configured to change the height of the head end 38 of litter frame 28. Foot end lift actuator 66*b* is configured to change the height of the foot end 40 of litter frame 28. When both of these actuators 66*a* and 66*b* are operated simultaneously and at the same speed, the height of litter frame 28 is raised or lowered without changing the general orientation of litter frame 28 with respect horizontal. When one or more of these actuators 66*a* and/or 66*b* are operated at different times and/or at different speeds, the orientation of litter frame 28 is changed with respect to horizontal. Lift actuators 66*a* and 66*b* are therefore able to tilt litter frame 28 to a variety of different orientations, including, but not limited to, a Trendelenburg orientation and a reverse-Trendelenburg orientation.

Gatch actuator 66*c* is adapted to raise and lower the joint that couples together the thigh section 46 and the foot section 48 of support deck 30, thereby raising and lowering the portion of the support deck 30 that is positioned close to the patient's knees. Fowler actuator 66*d* is adapted to raise and lower the head section (or Fowler section) 42 of the support deck 30.

Control panel 56 (FIG. 4) communicates with main controller 70 and is adapted to allow a user to control the various functions performed by main controller 70, including, but not limited to, the scale function and the exit detection function carried out by main controller 70 (and force sensors 54). The plurality of controls 58 of control panel 56 may be implemented as buttons, dials, switches, icons on a touchscreen, or other devices. Display 60 of control panel 56 may be a touchscreen that displays one or more controls and/or one or more control screens, some of which are discussed in greater detail below. Display 60 may comprise an LED display, OLED display, or another type of display.

Control system 62 of patient support apparatus 20 (FIG. 5) also includes camera 72, which may be a still camera or a video camera, depending upon the particular embodiment of patient support apparatus 20. Further, in some embodiments, control system 62 may include more than one camera 72. Regardless of the specific number, each camera 72 is positioned onboard patient support apparatus 20 at any suitable location that gives the camera 72 a field of view that encompasses the support deck 30. More specifically, the field of view of camera 72 is aimed such that it will include within its field of view the patient when the patient is positioned on support deck 30, as well as any objects that are positioned on top of the mattress positioned on support deck 32 (or that may be positioned elsewhere on support deck 32 or litter frame 28). Camera 72 is used by main controller 70 to monitor objects that are added and/or removed the patient support apparatus 20. As will be explained in greater detail below, this monitoring may be performed in conjunction with monitoring that is carried out by the scale system so that when an object is added or removed from support deck 30, this action is detectable both by the scale system and the camera 72. In some embodiments, patient support apparatus 20 may be constructed to include any of the cameras, as well as any of the functions and/or other structural components, of the patient support apparatuses disclosed in commonly assigned U.S. patent application Ser. No. 63/218,053 filed Jul. 2, 2021, by inventors Krishna Bhimavarapu et al. and entitled PATIENT VIDEO MONITORING SYSTEM, the complete disclosure of which is incorporated herein by reference. Other types of patient support apparatus functions/constructions and/or cameras may, of course, be used.

Object transceiver 74 (FIG. 5) is adapted to communicate with one or more objects 90 that are placed on patient support apparatus 20, such as on the support deck 30 (or on the mattress positioned on top of support deck 30). In some embodiments, object transceiver 74 is a conventional Bluetooth transceiver (classic or low-energy). In other embodiments, object transceiver 74 may be an ultra-wideband transceiver, a ZigBee transceiver, or another type of wireless transceiver. Regardless of the specific type of transceiver it is, object transceiver 74 is configured to wirelessly communicate with a similar type of transceiver that is positioned onboard, or integrated into, the object 90. Alternatively, object transceiver 74 may be configured to wirelessly communicate with an electronic tag 92 that is coupled to the object. The electronic tag 92 may be a conventional RFID tag, an ultra-wideband tag, and/or another type of electronic tag.

The particular types of objects 90 that transceiver 74 may be configured to communicate with can vary widely. In general, transceiver 74 is configured to communicate with any one or more of the following types of devices: exercise devices, heel care boots, IV stands and/or poles, ventilators, patient monitors (e.g. saturated oxygen ($Sp0_2$) monitors), vital sign detectors (e.g. heart rate, breathing rate, temperature), patient positioning devices (e.g. wedges, turning devices, pumps), ambient sensors (e.g. air temperature, air flow, light, humidity, pressure, altitude, sound/noise), sequential compression devices used to aid circulation and prevent blood clots, mattress pumps, chest tube collection canisters, wound vacuum machines, orthopedic equipment for traction, etc., and/or any other types of devices that are used in the treatment, monitoring, and/or rehabilitation of the patient. It will be understood that not all objects that are added to support deck 30 will include wireless communication abilities, and therefore transceiver 74 will not be able to communicate with all objects 90 that are added to patient support apparatus 20 (e.g. a book being read by the patient, a food tray containing food for the patient, etc.). However, as will be explained in greater detail below, controller 70 may be configured to instruct transceiver 74 to attempt to establish communication with an object 90 (and/or its tag 92) when it is added to patient support apparatus 20 as part of an object identification process, and/or as part of another process.

As was mentioned, in some embodiments, object transceiver 74 may be an ultra-wideband transceiver in some embodiments. In such embodiments, object transceiver 74 (and tag 92) may be constructed in the same manner as, and/or include any of the same functionality as, the ultra-wideband transceivers (and electronic tags) disclosed in the following commonly assigned U.S. patent applications (and/or patient support apparatus 20 may include any of the functions, components, and/or features of any of the patient support apparatuses disclosed in the following commonly assigned U.S. patent applications): Ser. No. 63/132,514 filed Dec. 31, 2020, by inventors Alexander Bodurka et al. and entitled PATIENT SUPPORT APPARATUS AND MEDICAL DEVICE NETWORKS; Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION; Ser. No. 63/161,175 filed Mar. 15, 2021, by inventors Krishna Bhimavarapu et al. and entitled EXERCISE DEVICE AND PATIENT SUPPORT APPARATUS; Ser. No. 63/193,777 filed May 27, 2021, by inventors Thomas Deeds et al. and entitled SYSTEM FOR ASSOCIATING MEDICAL DEVICE DATA; Ser. No. 63/245,245 filed Sep. 17, 2021, by inventors Kirby Neihouser et al., and entitled SYSTEM FOR LOCATING PATIENT SUPPORT APPARATUSES; Ser. No. 63/245,279, filed Sep. 17, 2021, by inventors Jerry Trepanier et al. and entitled PATIENT SUPPORT APPARATUSES WITH PATIENT MONITORING; and Ser. No. 63/245,289 filed Sep. 17, 2021, by inventors Madhu Sandeep Thota et al. and entitled PATIENT SUPPORT APPARATUS COMMUNICATION AND LOCATION SYSTEM; the complete disclosures of all of which are incorporated herein by reference.

In those embodiments where object transceiver 74 is a Bluetooth transceiver, object transceiver 74 may be configured to perform-in addition to the functions described herein-any of the functions of the Bluetooth transceivers disclosed in any of the commonly assigned U.S. patent applications that have already been incorporated herein by reference, as well as any of the Bluetooth transceivers disclosed in any of the following commonly assigned U.S. patent applications: Ser. No. 16/847,753 filed Apr. 14, 2020, by inventors Alexander Bodurka et al. and entitled PATIENT SUPPORT APPARATUSES WITH NURSE CALL AUDIO MANAGEMENT; Ser. No. 63/26,937 filed May 19, 2020, by inventors Alexander Bodurka et al. and entitled PATIENT SUPPORT APPARATUSES WITH HEADWALL COMMUNICATION; and Ser. No. 63/193,778 filed May 27, 2021, by inventors Krishna Bhimavarapu et al. and entitled PATIENT SUPPORT APPARATUS AND HEADWALL UNIT SYNCHING; the complete disclosures of all of which are incorporated herein by reference.

Network transceiver 68 (FIG. 5) is adapted to communicate with a hospital's local area network 78. In some embodiments, network transceiver 68 is a conventional WiFi transceiver (i.e. IEEE 802.11 . . . ) adapted to wirelessly communicate with one or more wireless access points 80 of a hospital's local area network 78. In other embodiments, network transceiver 68 may be a wireless transceiver that uses conventional 5G technology to communicate with network 78, one or more servers hosted thereon, and/or other devices. In some embodiments, network transceiver 68 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In other embodiments, network transceiver 68 may be a conventional Ethernet transceiver electrically coupled to a conventional Ethernet port (i.e. RJ-45 jack, or the like) built into patient support apparatus 20 that allows a conventional Ethernet cable to be coupled to the patient support apparatus 20. In these embodiments, patient support apparatuses 20 may be coupled to the hospital's local area network 78 by a wired connection. In still other embodiments, patient support apparatus 20 may have both wired and wireless transceivers 68. Still further, in some embodiments, transceiver 68 may take on yet a different form (e.g. a wireless ZigBee transceiver, a Bluetooth transceiver, etc.).

Patient support apparatus 20 uses transceiver 68, in some embodiments, to communicate with a patient support apparatus server 82. Patient support apparatus server 82 may be adapted to receive status information from patient support apparatuses 20 and distribute that information to one or more other servers and/or other devices coupled to local area network 78. In at least one embodiment, patient support apparatus server 82 includes a caregiver assistance application 84 that is adapted to communicate information between both patient support apparatuses 20 and one or more portable electronic devices 86. The portable electronic devices 86 includes, but are not limited to, smart phones, tablets, laptops, Computers on Wheels (COWs), and the like. Each portable electronic device 86 includes a display 88 on which various screens may be displayed, including, in some embodiments, portions of one or more of the screens discussed below. In some embodiments, caregiver assistance application 84 allows authorized users to remotely configure and remotely control various aspects of the patient support apparatuses 20 using their portable computing device 86. Still further, caregiver assistance application 84 may be adapted to display information about the scale systems of the patient support apparatuses 20, including any of the information discussed in greater detail below regarding the scale system.

In any of the embodiments disclosed herein, caregiver assistance application 84 may be configured to include any of the same features or functions as—and/or to operate in any of the same manners as—the caregiver assistance software applications described in the following commonly assigned patent applications: U.S. patent application Ser. No. 62/826,097, filed Mar. 29, 2019 by inventors Thomas Durlach et al. and entitled PATIENT CARE SYSTEM; U.S. patent application Ser. No. 16/832,760 filed Mar. 27, 2020, by inventors Thomas Durlach et al. and entitled PATIENT CARE SYSTEM; and/or PCT patent application serial number PCT/US2020/039587 filed Jun. 25, 2020, by inventors Thomas Durlach et al. and entitled CAREGIVER ASSISTANCE SYSTEM, the complete disclosures of which are all incorporated herein by reference. That is, server 82 may be configured to share with one or more electronic devices 86 any of the information shared with the electronic devices disclosed in these aforementioned patent applications. Thus, for example, server 82 may be configured to not only share the location of patient support apparatuses 20 (and any devices that may be associated with them) with electronic devices 86, but it may also forward any of the data generated by patient support apparatuses 20 to the electronic devices 86, thereby letting the caregivers associated with these patient support apparatuses 20 know if, for example, the patient has exited patient support apparatus 20, what the patient's current weight is, whether one or more objects have been added to, and/or removed from, the patient support apparatus 20, and/or the identity and/or visual images of the object(s). Alternatively, or additionally, patient support apparatus server 82 may forward other patient support apparatus status data (e.g. current siderail position, bed exit status, brake status, height status, scale data, etc.) and/or caregiver rounding information (e.g. when the last rounding was performed for a particular patient, when the next rounds are due, etc.), and/or object data from any objects supported on patient support apparatus 20 to one or more electronic devices 86, thereby providing the caregivers associated with the devices 86 a consolidated portal (e.g. a single software application) for sharing this various information.

In some embodiments, patient support apparatus server 82 is also configured to determine the location of each patient support apparatus 20, or receive the location of each patient support apparatus 20 from the patient support apparatuses 20. In some embodiments, patient support apparatus server 82 determines the room number and/or bay area of each patient support apparatus 20 that is positioned within a room, as well as the location of patient support apparatuses 20 that are positioned outside of a room, such as, those that may be positioned in a hallway, a maintenance area, or some other area. In general, patient support apparatus server 82 may be configured to determine the position of any patient support apparatus 20 by communicating with one or more nearby wall units (not shown). Further details regarding several manners in which patient support apparatus 20 may be constructed in order to carry out such location communication, as well as the construction and/or operation of such wall units, are disclosed in the following commonly assigned U.S. patent applications: Ser. No. 63/245,245 filed Sep. 17, 2021, by inventors Kirby Neihouser et al., and entitled SYSTEM FOR LOCATING PATIENT SUPPORT APPARATUSES; Ser. No. 63/245,289 filed Sep. 17, 2021, by inventors Madhu Sandeep Thota et al. and entitled PATIENT SUPPORT APPARATUS COMMUNICATION AND LOCATION SYSTEM; Ser. No. 63/26,937 filed May 19, 2020, by inventors Alexander Bodurka et al. and entitled PATIENT SUPPORT APPARATUSES WITH HEADWALL COMMUNICATION; and Ser. No. 63/193,778 filed May 27, 2021, by inventors Krishna Bhimavarapu et al. and entitled PATIENT SUPPORT APPARATUS AND HEADWALL UNIT SYNCHING; the complete disclosures of all of which have already been incorporated herein by reference.

It will be understood that the architecture and content of local area network 78 will vary from healthcare facility to healthcare facility, and that FIG. 5 merely shows a generic example of the type of network a healthcare facility may be employ. Typically, one or more additional servers will be hosted on network 78 and one or more of them may be adapted to communicate with patient support apparatus server 82. For example, an electronic health record server will typically be present in any healthcare facility, and in some embodiments discussed herein, it will be in communication with patient support apparatus server 82 in order to receive patient data that is to be recorded in a patient's health record (e.g. weight readings taken from the scales built into patient support apparatuses 20; therapies provided to patients using a powered mattress onboard patient support apparatuses 20, data from one or more tags and/or objects 90 that are positioned onboard the patient support apparatus 20, etc.).

Figure 6:
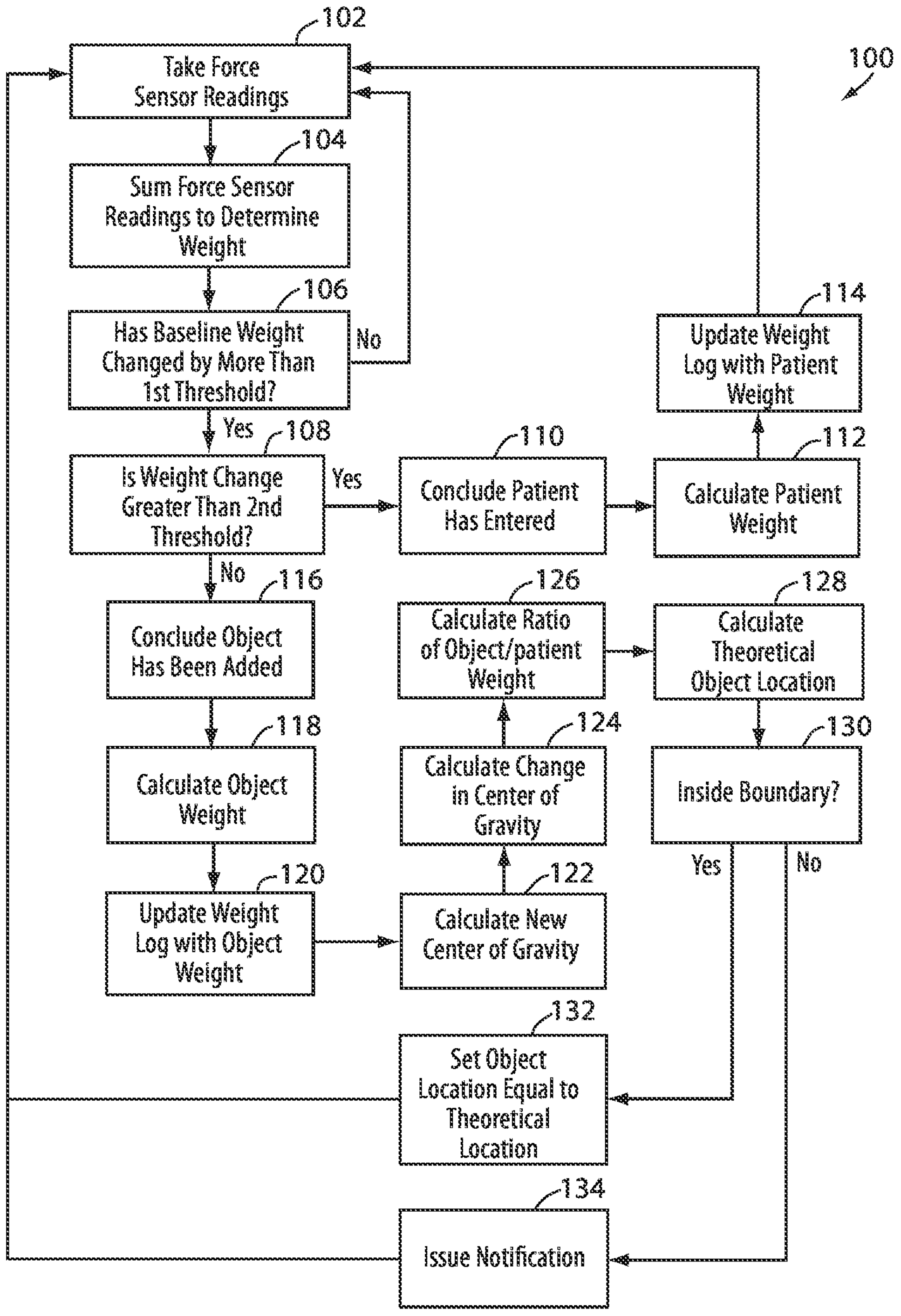
FIG. 6 is a flow diagram of an automatic weight detection algorithm that may be implemented by the patient support apparatus.

FIG. 6 illustrates one example of an automatic weight detection algorithm 100 that may be executed by main controller 70 of patient support apparatus 20. In general, and as will be discussed in greater detail below, algorithm 100 causes controller 70 to automatically detect the addition and/or removal of objects from patient support apparatus 20, to display one or more screens on display 60, and to take one or more actions automatically in response to the detection of an object being added/removed from patient support apparatus 20.

Algorithm 100 begins at step 102 where controller 70 receives readings from each of the force sensors 54. At step 104, controller 70 sums together the force sensor readings received at step 102. The result of this summation is a measurement of the total weight currently onboard the scale system of patient support apparatus 20. Although this total weight includes the weight of the litter frame 28, the support deck 30, a mattress (if present), any bedding (if present), etc., the weight readings from structures and objects are typically zeroed out of the scale system when algorithm 100 initially starts executing. That is, in some embodiments, the scale system is zeroed as a precursor to the execution of algorithm 100. In such situations, algorithm 100 automatically commences running after the scale system has been zeroed. This zeroing process typically ensures that no patient, as well as no objects other than standard objects (e.g. mattress, bedding, pillow, etc.), are present on the patient support apparatus 20 when algorithm 100 is initially executed. Therefore, it will be understood that objects 90 refer to objects other than the standard objects that are always, or substantially always, on patient support apparatus 20 (e.g. mattress, bedding, pillow, etc.), and that algorithm 100 will therefor initially begin when no objects 90 are on patient support apparatus 20. However, algorithm 100, as will be discussed in more detail below can still operate in the manner described below even if one or more objects have been placed on patient support apparatus 20 initially.

After summing the total forces sensed at step 104 (FIG. 6), controller 70 proceeds to step 106 where it determines if a baseline weight has been changed by more than a first threshold. The baseline weight is established over the course of a number of consecutive weight readings (step 102) where there is no substantial variation in the weight sensed by force sensors 54. In other words, controller 70 automatically established a baseline weight reading when a consecutive series of weight readings from force sensors 54 indicate that nothing has been added or removed from patient support apparatus 20, or the patient (if present) has generally stopped movement for a period of a few seconds or so. As a result, the very first time controller 70 performs step 106, there may not be an established baseline weight reading, in which controller 70 returns to step 102 and takes another weight reading. However, if sufficient weight readings have been taken at step 102 to establish a baseline weight reading, controller 70 proceeds to step 108 if the force sensors 54 measure a weight reading that differs from the baseline reading by more than a first threshold. On the other hand, if the weight readings do not differ by the baseline weight reading by more than the first threshold, then controller 70 returns to step 102 and takes another set of weight readings. In some embodiments, the initial baseline weight reading may be set equal to the sum of the force sensors 54 at the time the scale was zeroed.

It will be understood that the frequency at which controller 70 takes new weight readings at step 102 may vary widely from embodiment to embodiment. In some embodiments, controller 70 takes new weight readings every five or so milliseconds. In other embodiments, the new weight readings may be taken even more often, or in other cases, less often. It will also be understood that any of steps 102-108 of algorithm 100 may be performed in any of the same manners as, or include any of the same features and/or functions as, the baseline weight processing and/or threshold comparison steps of the following commonly assigned U.S. patent references: U.S. Pat. No. 10,357,185 issued to Marko Kostic et al. on Jul. 23, 2019, and entitled PERSON SUPPORT APPARATUSES WITH MOTION MONITORING; U.S. Pat. No. 11,33,233 issued to Michael Hayes et al. on Jun. 15, 2021, and entitled PATIENT SUPPORT APPARATUS WITH PATIENT INFORMATION SENSORS; and U.S. patent application Ser. No. 16/992,515 filed Aug. 13, 2020, by inventors Kurosh Nahavandi et al. and entitled PATIENT SUPPORT APPARATUS WITH EQUIPMENT WEIGHT LOG, the complete disclosures of all of which are incorporated herein by reference.

As noted, if controller 70 determines at step 106 that the change in the baseline weight reading at step 106 is greater than first threshold, then controller 70 proceeds to step 108. The particular threshold used at step 106 may be varied in different embodiments (or step 106 may be omitted in some embodiments). In some embodiments, the first threshold is around half of a kilogram, although other thresholds may be used. In general, the purpose of step 106 is to ignore minor weight changes that are likely transitory and not of any potential significance to a caregiver (e.g. a patient picks up a book or magazine and adds it to the patient support apparatus 20, or a food tray is placed on the patient support apparatus 20, or the like).

At step 108 (FIG. 6), controller 70 compares the change from the baseline to a second threshold value that is larger than the first threshold value. In some embodiments, the second threshold value may be in the range of approximately twenty to forty kilograms. The purpose of step 108 is to distinguish between weight changes attributable to the patient entering or exiting the patient support apparatus and weight changes attributable to an object being added or removed from the patient support apparatus 20. Weight changes greater than the second threshold are presumed to be due to a patient entering/exiting, while weight changes less than the second threshold are presumed to be due to an object being added or removed. Different weight thresholds can, of course, be used, depending upon whether patient support apparatus 20 is intended for use with pediatric patients and/or for use with heavy equipment that may be placed on patient support apparatus 20.

In some embodiments, the threshold used at step 106 and/or at step 108 may be customizable by a user. That is, patient support apparatus 20 may be configured to display a screen that allows the user to set higher or lower values for the first threshold of step 106 and/or for the second threshold of step 108.

As shown in FIG. 6, if controller 70 determines at step 108 that the weight change is greater than the second threshold, controller 70 concludes at step 110 that the weight change is due to a patient entering/exiting patient support apparatus 20, and controller 70 then proceeds to step 112. However, if the weight change is less than the second threshold, controller concludes at step 116 that an object has been added/removed. From step 116, controller proceeds to step 118.

Before turning to step 118, if controller determines at step 110 that a patient has entered or exited patient support apparatus 20, controller 70 thereafter calculates the patient's weight. The patient's weigh will be equal to the change from the baseline weight (calculated at step 106 and used at steps 106 and 108). In other words, the change in the patient's weight is set by controller 70 to be equal to the weight change from the baseline weight reading that was established just prior to the patient entering/exiting patient support apparatus 20. In some embodiments, after recording the patient's weight at step 112, the patient's weight is entered into a weight log maintained by controller 70 and stored in memory 76. From step 114, controller 70 returns back to step 102 and proceeds in the manner previously described (using a new baseline weight reading that has changed by the patient's weight).

At step 118 (FIG. 6), controller 70 concludes that the change in weight from the baseline reading is due to an object 90 being added or removed from the patient support apparatus 20. After step 118, controller 70 updates the weight log with the weight of the object 90. The weight log updated at step 120 is the same weight log updated at step 114. The updating of the weight log with an object's weight and/or a patient's weight remains in the weight log until a user manually instructs controller 70 to remove the item from the weight log, or controller 70 automatically determines that an article was removed (or the patient exited) from patient support apparatus 20 (as detected during the execution of algorithm 100).

After completing step 120, controller 70 moves to step 122 where it computes a new center of gravity of the weight supported on force sensors 54. Although not shown in FIG. 6, controller 70 repetitively calculates the center of gravity of the weight on force sensors 54. In some embodiments, this center of gravity calculation may be done as part of step 104, or it may be done elsewhere. Regardless of where the calculation is performed, controller 70 is configured to compute a first center of gravity before a weight change above the first threshold is detected at step 106, as well as to compute a second center of gravity after the weight change above the first threshold is detected (as well as successive additional centers of gravity). The second center of gravity is computed at step 122, and at step 124 controller 70 compares the first and second centers of gravity and determines how much the center of gravity has shifted due to the object 90 being place on patient support apparatus 20.

At step 126, controller 70 calculates the ratio of the object's weight to the patient's weight (if present on patient support apparatus 20). If there is no patient currently present on patient support apparatus 20, controller 70 moves to step 128 and determines the location of the added object 90. If there is a patient currently present on patient support apparatus 20, controller uses the ratio calculated at step 126 to calculate a theoretical location of the object 90 at step 128. Controller 70 therefore computes a location of the added object 90 at step 128 regardless of whether a patient is present on patient support apparatus 20 or not. However, if no patient is present, controller 70 concludes that the calculated location of the object 90 is the actual location of the object. On the other hand, if a patient is currently positioned on patient support apparatus 20, then controller 70 initially concludes that the calculated location of the object 90 is only a theoretical location of the object. This is because there is a possibility that the patient moved while the object 90 was placed on the patient support apparatus 20, and, as a consequence, there is a possibility that the change in the center of gravity calculated at step 124 may not be entirely due to the addition of the object 90, but instead may be partially due to movement of the patient. In this case, the calculated location of the added object 90 may be in error.

Regardless of whether the calculation made at step 128 (FIG. 6) is a calculation of an actual location of the object or a theoretical location of the object 90, controller 70 determines the actual and theoretical location in the same manner. Specifically, it looks at the weight of the object (which is equal to the change from the baseline weight detected at step 106), the new center of gravity (calculated at step 122), and determines what location the object must be in in order for it to have caused the measured change in the center of gravity, given the object 90's actual and relative weight. In other words, for example, if controller 70 sees that the center of gravity shifted two inches to the left side of patient support apparatus 20 and three inches to the foot end 40 after object 90 was placed on patient support apparatus, controller 70 uses the known weight of the object (as well as the known weight of the patient) to determine what position object 90 must have been placed in in order to cause the two inch shift to the left side and three inch shift to the foot end of the calculated center of gravity. In some embodiments, controller 70 computes the ratio of the weight of the object 90 to the total weight detected by patient support apparatus 20 at step 126 and uses that ratio at step 128 instead of, and/or in addition to, the weight ratio of object 90 to the patient.

After calculating the location of object 90 at step 128 (FIG. 6), controller 70 moves to step 130 where it determines whether or not the calculated location of object 90 is inside or outside of a boundary. The boundary, in some embodiments, is set equal to the perimeter of the mattress and/or the perimeter of support deck 30. Alternatively, the boundary may be set equal to the perimeter of litter frame 28. The purpose of the boundary is to determine whether or not the calculated location of the object 90 is on the patient support apparatus 20, or off in space. If it is off in space (i.e. not on patient support apparatus 20), then controller 70 concludes that the patient must have moved during the addition of the object 90, and that the patient movement is responsible for at least a portion of the change in the center of gravity (because the addition of the object 90 could not account for all of the change in the center of gravity). In other words, controller 70 knows that, if the theoretical location is determined to be at a location off of patient support apparatus 20, then the change in the center of gravity must have been due to something other than the addition of the object 90.

Figure 17:
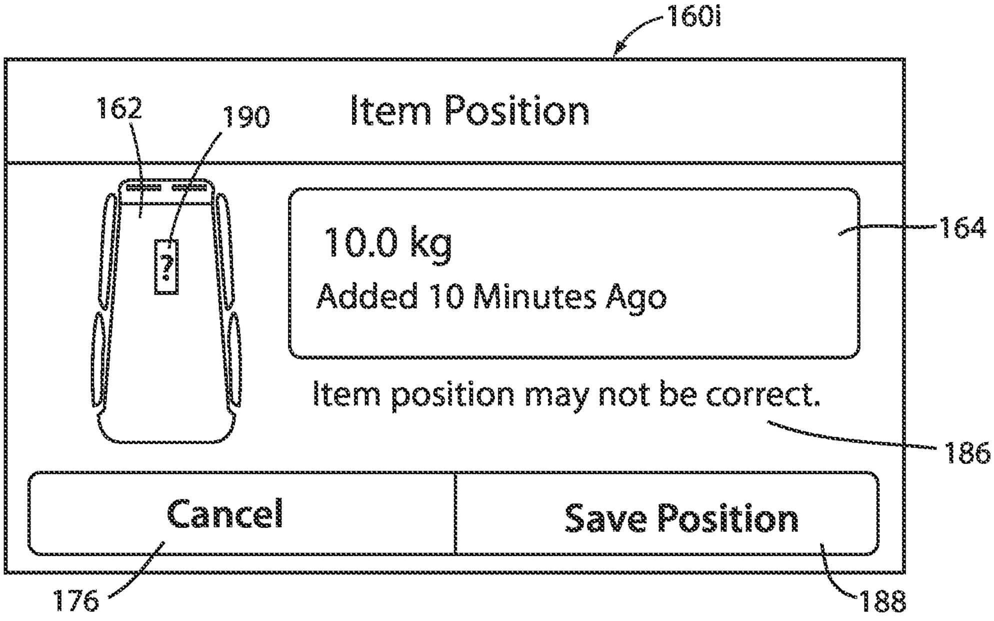
FIG. 17 is a tenth example of the weight log screen that may be displayed when the scale system determines that the location of an object is uncertain.

Accordingly, if controller 70 determines that the calculated location is outside of the boundary at step 130, it moves to step 134 and issues a notification to the user. The notification may take on a variety of different forms. In at least one embodiment, the notification includes the display of a message on display 60 indicating that the location of the object cannot be determined. One example of such a notification is shown in FIG. 17 and discussed in more detail below. If controller 70 determines at step 130 that the location in inside of the boundary, then controller 70 proceeds to step 132 where it concludes that the actual location of the object is equal to the location calculated at step 128. In other words, at step 132, controller 70 concludes that the theoretical location is accurate. Controller 70 is also configured to store the location of the object 90 in the log as part of step 132.

After completing either step 132 or 134, controller 70 returns to step 102 and performs another iteration of algorithm 100. In some embodiments, algorithm 100 cycles continuously for as long as patient support apparatus 20 is receiving power. The log that is updated at steps 114 and 120 is retained in memory until the user either manually resets it, or the patient and/or object(s) 90 in the log are removed from the patient support apparatus 20.

It will be understood that a number of modifications can be made to algorithm 100 without departing from the spirit of the present disclosure. For example, in at least one modified embodiment, instead of determining a ratio at step 126 and using that ratio to calculate the location of an added object 90, controller 70 may be configured to determine the location of the added object by looking at the individual force sensor readings in the moment immediately before the object 90 was added and the moment immediately after the object was added. The difference in the readings for each force sensor 54 can then be used to calculate the center of gravity of the added object 90, which is considered the location of the object by controller 70. For example, assume that each of the four force sensors are measuring a 25 kg load prior to object 90 being added. And also assume that, immediately after object 90 is added, the two head end force sensors 54 each detect a 26 kg load, the foot end right force sensor 54 detects a 26 kg load, and the foot end left force sensor 54 detects a 29 kg load. In such a case, controller 70 calculates the difference in each of the force sensor readings, which yields a 1 kg difference for all of the force sensors 54 with the exception of the foot end left force sensors 54, which yields a 4 kg difference. Controller 70 then calculates the center of gravity of the three 1 kg force sensor readings and the single 4 kg force sensor reading. This calculation yields the center of gravity of the object 90.

Algorithm 100 may also, or alternatively, be modified such that instead of calculating the theoretical location of the object's location at step 128, controller 70 instead looks at the change in the overall center of gravity (patient weight and object weight) determined at step 124 and the ratio determined at step 126 and concludes that the object's location cannot be determined with sufficient confidence if the change of step 124 and/or the ratio of step 126 meet certain thresholds. For example, if the center of gravity moves more than a threshold at step 124 and/or the object's weight is below a specific weight limit, controller 70 may be configured to conclude that the object's location cannot be confidently determined. In such embodiments, controller 70 may issue a notice to the user indicating that the location of the object cannot be determined with confidence, and that he or she should remove the object and place it on patient support apparatus 20 again.

It will be understood that memory 76 contains the positions of each of the force sensors 54 positioned onboard patient support apparatus 20. Further, the positions of each of these force sensors 54 is known within a coordinate frame of reference that is the same coordinate frame of reference used to calculate the centers of gravity discussed herein. The boundary used at step 130 is also defined in memory 76 in a coordinate frame of reference that is the same as, or that can be converted to, the same coordinate frame of reference in which the centers of gravity are calculated.

It will also be understood that algorithm 100 (FIG. 6) is used by controller 70 when an object 90 is removed from, and/or when the patient exits, patient support apparatus 20. That is, algorithm 100 works not only for increases in forces sensed by force sensors 54, but it also functions in the same manner for decreases in the forces sensed by force sensors 54. When detecting the removal of object 90 (or the exiting of the patient), controller 70 updates the log at step 114 and step 120 by removing the entity (either the patient or an object 90) from the log, rather than adding them to the log. When detecting the removal of objects, step 130 of algorithm 100 may be modified slightly so that controller 70 compares the theoretical location of the removed object 90 to the location(s) of the object(s) 90 stored in the log, rather than comparing a theoretical location to a boundary. Controller 70 searches the object(s) in the log at step 130 for an object 90 stored therein that has the same location as, or nearly the same location as, the theoretical location of the removed object 90. If it finds a match, it proceeds to step 132 and removes the matching object 90 from the weight log. If it does not find a match, it proceeds to step 134 and issues a notification to the user indicating that the location of the removed object could not be determined. In some embodiments, controller 70 is configured to conclude a match exists if the weight and/or location of a removed object 90 are within a threshold value of the weight and/or location of an object stored in the weight log. If there are multiple objects in the weight log that are within the threshold value of the location and weight, controller 70 may be configured to remove the object from the weight log that is closest to the weight and location of the removed object 90.

From the foregoing description, it can be seen that algorithm 100 automatically detects the addition and removal of objects. There is no need for a user to manually press on a button or other control when he or she adds or removes an object 90 and wants to update the log to reflect the addition or removal of that object 90. In some embodiments, algorithm 100 may be modified such that its automatic detection of added or removed objects, and/or its automatic updating of the log of these objects, may be performed in any of the manners disclosed in commonly assigned U.S. patent application Ser. No. 16/992,515 filed Aug. 13, 2020, by inventors Kurosh Nahavandi et al. and entitled PATIENT SUPPORT APPARATUS WITH EQUIPMENT WEIGHT LOG, the complete disclosure of which has already been incorporated herein by reference. Thus, it will be understood that algorithm 100 may be supplemented by, replaced by, and/or modified by any of the features or functions of the scale system disclosed in the aforementioned '515 patent application.

As controller 70 executes algorithm 100, it may display a number of different screens on display 60 that are designed to inform the caregiver of the operation of algorithm 100, as well as to keep the user clearly informed of what object(s) 90 are currently in the weight log and what object(s) are not in the weight log. Several examples of these screens are shown herein in FIGS. 7-17, and these will now be described in greater detail.

Figure 7:
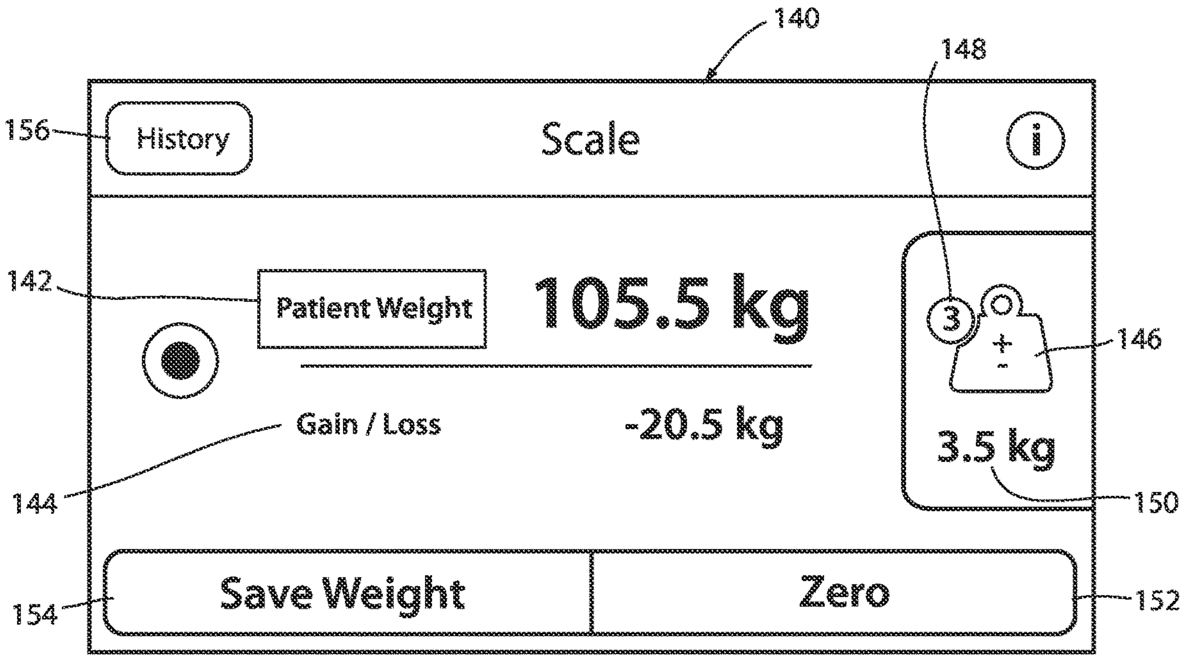
FIG. 7 is an illustrative scale screen displayable on the control panel of FIG. 4.

FIG. 7 illustrates a scale screen 140 that controller 70 may be configured to display on display 60 in response to the user pressing on scale control 58*c*. Scale screen 140 includes a patient weight indicator 142, a gain/loss indicator 144, a weight log icon 146, an object number 148, an object total weight indicator 150, a zero control 152, a save weight control 154, and a scale history control 156. Patient weight indicator 142 indicates the currently measured patient weight, which is determined by subtracting the weight of any objects 90 in the weight log from the current total weight on force sensors 54 (after the force sensors have been zeroed). Gain/loss indicator 144 indicates the total patient weight loss or gain since the patient's weight was last saved by the user. Controller 70 is configured to store in memory 76 each of the patient weight readings that a caregiver saves for a particular patient. The gain/loss indicator displays the difference between the current patient weight and the last saved patient weight reading in memory 76.

Log icon 146 is an icon that corresponds to the weight log discussed above with respect to algorithm 100. That is, log icon 146 corresponds to the weight log that controller 70 maintains of all of the objects 90 that may be added to the litter frame 28 of patient support apparatus 20. If the user presses on weight log icon 146, controller 70 is configured to display a screen that provides more information about the weight log, such as a screen like those shown in FIGS. 8-11, 13, 15, and/or 16. Object number 148 indicates the number of objects 90 that are currently in the weight log. Thus, in the example shown in FIG. 7, the weight log currently has three objects 90 recorded therein that are positioned on litter frame 28. Weight total indicator 150 indicates the total weight of the objects 90 currently stored in the weight log. Thus, in the example of FIG. 7, the three objects 90 stored in the weight log have a total cumulative weight of 3.5 kg, as indicated by indicator 150.

Screen 140 (FIG. 7) also includes a save weight control 154 and a zero control 152. If the user presses on the save weight control 154, controller 70 is configured to store the currently measured patient weight (as indicated by indicator 142) within memory 76. That stored patient weight is then used as a baseline for future patient weight readings when controller 70 computes the value to be shown by the gain/loss indicator 144. In other words, when the user presses the save weight control 154, controller 70 zeroes the gain/loss indicator 144. In the example of FIG. 7, after the user presses the save weight control 154, controller 70 would change indicator 144 to zero and thereafter only show non-zero values if the patient's weight deviated from 105.5 kg.

If the user presses on zero control 152 (FIG. 7), controller 70 is configured to zero (i.e. tare) the scale system. That is, in response to control 152 being activated by a user, controller 70 takes a snapshot of the current total weight readings recorded by force sensors 54 and considers that weight value to be equal to the empty weight of patient support apparatus 20 (i.e. the weight on the scale system when no patient is present and no objects of interest are present). Typically, a caregiver uses control 152 to zero the scale system when the patient is absent, but a mattress, a pillow, bedding, and other standard items (if any) are present on the patient support apparatus 20. In this manner, the weight of the mattress, pillow, bedding, etc., as well as the structural weight of the support deck 30 and litter frame 28, are zeroed out. In some embodiments, after the user has zeroed the scale system using control 152, controller 70 is configured to erase any items that were stored in the weight log.

Scale screen 140 also includes a scale history control 156. When a user presses on control 156, controller 70 is configured to display a different screen that graphically shows a history of the patient's weight readings. The graph may have time on the X-axis and the patient's weight on the Y-axis. The patient weight history screen gives the caregiver a visual overview of the fluctuations in the patient's weight while they were assigned to that particular patient support apparatus 20. In some embodiments, scale history control 156 is displayed in a first color (and/or with a first configuration) when there is data contained within the scale history, and in a second color (and/or with a second configuration) when there is no data contained within the scale history. Thus, for example, if the caregiver has never taken a weight reading of the patient, controller 70 might display control 156 with a first color until the caregiver takes a first patient weight reading, at which point controller 70 will switch to displaying control 156 in a second color so that the user knows that previous patient weight readings have been taken.

Figure 8:
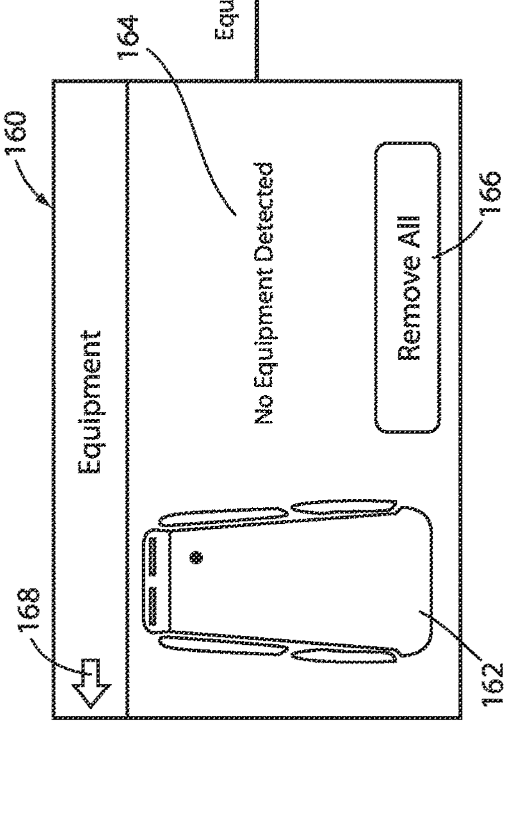
FIG. 8 is a first example of a weight log screen illustrating a situation in which no objects are detected on the patient support apparatus.
Figure 9:
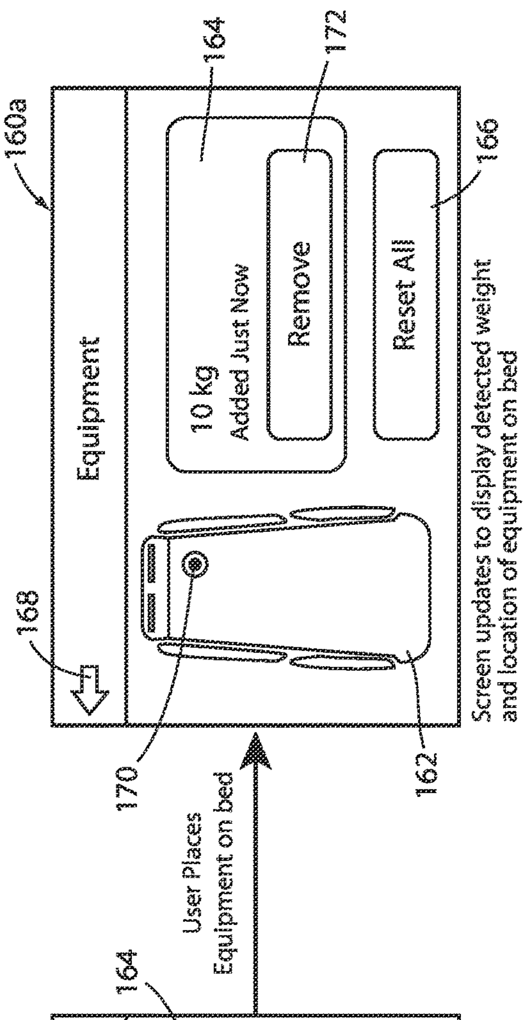
FIG. 9 is a second example of the weight log screen illustrating a situation where a 10 kg weight has been recently added to the patient support apparatus.
Figure 10:
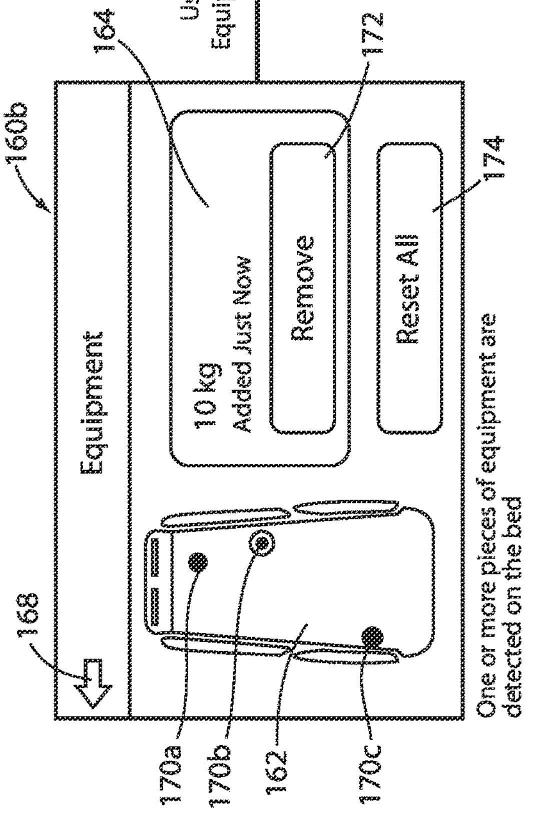
FIG. 10 is a third example of the weight log screen illustrating a situation where a third object has been recently added to the patient support apparatus.

FIG. 8 illustrates a weight log screen 160 that may be displayed in response to a user pressing on weight log icon 146 (FIG. 7). The particular weight log screen 160 shown in FIG. 8 corresponds to the situation where the weight log is empty. FIG. 9 illustrates another weight log screen 160*a* that corresponds to a situation where a single object 90 has been stored in the weight log, and FIG. 10 illustrates yet another weight log screen 160*b* that corresponds to a situation where the weight log includes three objects 90 stored therein. Further variations of screen 160 will be displayed by controller 70 when still other numbers of objects 90 are detected (and/or when the objects are detected in different locations).

Weight log screen 160 (FIG. 8) includes a patient support apparatus icon 162, a message area 164, a "remove all" control 166, and a back control 168. Patient support apparatus icon 162 is depicted to look generally similar to the actual look of patient support apparatus 20, and is shown in a manner in which the patient support surface is visible. As will be discussed in greater detail below, controller 70 is configured to position object icons on patient support apparatus icon 162 at locations that correspond to the actual locations of objects 90 positioned on the actual patient support apparatus 20.

The message area 164 provides information to the user that is relevant to the current status of the patient support apparatus 20 and/or the weight log. In the particular example of FIG. 8, message area 164 includes the message "no equipment detected." Controller 70 displays this message when the weight log is empty. The "remove all" control 166 of weight log screen 160 (FIG. 8) is ghosted, or otherwise inoperative, in the situation shown in FIG. 8. This is because the "remove all" control 166 is used when the caregiver wishes to remove all objects 90 from the weight log, and in the situation shown in FIG. 8, the weight log is already empty. It is therefore inoperative on screen 160. The back control 168 is used by the caregiver when he/she wishes to return to the previously displayed screen and/or the scale screen 140 (FIG. 7). That is, controller 70 is configured to switch to displaying the previously displayed screen or scale screen 140 in response to the user pressing on back control 168.

FIG. 9 illustrates another weight log screen 160*a* that may be displayed by controller 70 when a single object 90 has been detected on patient support apparatus 20. In some embodiments, controller 70 may be configured to automatically display screen 160*a* whenever an object 90 is first added to patient support apparatus 20 and detected by the scale system. In such embodiments, controller 70 is configured to automatically change whatever screen it was previously displaying to the object weight log 160*a*. In some of such embodiments, controller 70 may also be configured to display screen 160*a* for only a limited amount of time if the caregiver does not press any of the controls on screen 160*a* for that time period. Controller 70 is also configured to display screen 160*a* automatically in response to a user pressing on weight log icon 146 (FIG. 7). Controller 70 may also be configured to display screen 160*a* in response to other triggers.

Weight log screen 160*a* (FIG. 9) differs from weight log screen 160 in that an object has been detected by the scale system. As a result of detecting this object, controller 70 has also calculated the location of this object (at, for example, step 132 of algorithm 100) and added an object icon 170 to the patient support apparatus icon 162. Controller 70 has positioned the object icon 170 on the patient support apparatus icon 162 at the same location that it has detected the actual object 90 to be positioned on patient support apparatus 20. Controller 70 is also configured to display additional information in message area 164 about at least one of the objects 90 that have been added to patient support apparatus 20. Thus, in the example of FIG. 9, controller 70 displays in message area 164 the message "10 kg—added just now." Other messages may, of course, be used. However, the amount of weight of the object 90 and the time at which it was added are desirably communicated to the user in some manner using the various weight log screens 160.

In response to the weight log including at least one object 90, controller 70 is configured to add a "remove" control 172 (FIG. 9) within the message area 164. The remove control 172 is used by a caregiver when he or she wishes to remove an object 90 from the weight log. If there are more than one objects 90 in the weight log, controller 70 is configured to display multiple object icons 170 on patient support apparatus 20, and the caregiver must first select which one of these multiple objects he or she would like to remove. In some embodiments, the caregiver selects the object 90 that is to be removed by tapping on the object icon 170 corresponding to the object 90 that he or she wishes to remove. After selecting the desired object 90 for removal, the user presses the remove control 172. Controller 70 then checks the outputs from the force sensors 54 to ensure that the caregiver has actually removed the selected object. In some embodiments, controller 70 is configured to give the caregiver a set amount of time, such as thirty seconds or so, to remove the selected object. Other time periods can, of course, be used. Once controller 70 detects that the object 90 has actually been removed from the patient support apparatus 20, and that the removed object is from the same location as the object icon 170, controller 70 changes weight log screen 160*a* such that the object icon 170 of the removed object 90 no longer appears on the patient support apparatus icon 162. In the example of FIG. 9, if the caregiver removes the object 90 corresponding to object icon 170, controller 70 will return to displaying the weight log screen 160 of FIG. 8, which includes no object icons 170 on it.

If the user presses on the remove control 172 (FIG. 9) but fails to remove the object 90 within the given time period, or if controller 70 detects that the removed object was in a different location than (or had a different weight than) the selected object icon 170, controller 70 is configured display an error message on screen 160*a*. The error message may differ for each of these situations. That is, if the user fails to remove an object within the time period, controller 70 may display a first error message indicating that no object has been removed, and the weight log will therefore not be updated to include any object removal. On the other hand, if the user removes an object 90 from a different location or of a different weight, controller 70 may display a second error message informing the user that the object 90 was removed from a different location (or of a different weight) and requesting that they confirm that they have removed the correct object, that they specify that a different object icon 170 corresponds to the removed object, and/or that they return the object back to the patient support apparatus 20 and remove it again. Still other messages for these situations can, of course, be displayed.

FIG. 10 illustrates another example of weight log screen 160*b* that may be displayed by controller 70 on display 60. Weight log screen 160*b* shows an example of a situation where three objects 90 are currently positioned on the patient support apparatus 20. The locations of these three objects 90 correspond to the locations of the three object icons 170*a-c* shown in FIG. 10. Message area 164 of weight log screen 160*b* shows additional information about a selected one of the object icons 170*a-c*. That is, controller 70 is configured to allow a user to tap on any of the three object icons 170*a-c* and display additional information about the object 90 that corresponds to the selected object icon. In general, the additional information identifies the weight of the object 90 and information regarding the time at which the object was added. In the particular example shown in FIG. 10, the caregiver has selected the object icon 170*a*, and controller 70 is displaying in message area 164 data indicating that the object 90 corresponding to icon 170*a* was added "just now" and that it weighs ten kilograms.

In situations such as shown in FIG. 10 where there are multiple objects 90 positioned on patient support apparatus 20, and thus multiple object icons 170 displayed on patient support apparatus icon 162, controller 70 is configured to add a "reset all" or a "remove all" control 174 (these two terms are used interchangeably). The "reset all" control 174 allows a caregiver to remove all of the objects 90 within the weight log all at once. If the user presses on "reset all" control 174, controller 70 looks for reductions in the weight detected by force sensors 54, as well as the locations of those weight reductions. If those weight reductions and their associated locations correspond to the weights and locations of the objects 90 stored in the weight log, controller 70 removes all of the objects 90 from the weight log and returns to displaying a weight log screen like screen 160 of FIG. 8. If the weight reductions detected by force sensors 54 don't correspond to the weights of the objects in the weight log, and/or the location of the weight reductions doesn't correspond to the locations of the objects 90 stored in the weight log (or if the force sensors 54 don't detect any weight reductions at all within a time period after the "reset all" control 174 is activated), controller 70 issues an error message to the caregiver. The error message may be similar to any of the error message discussed above, or it may take on still other forms.

Figure 11:
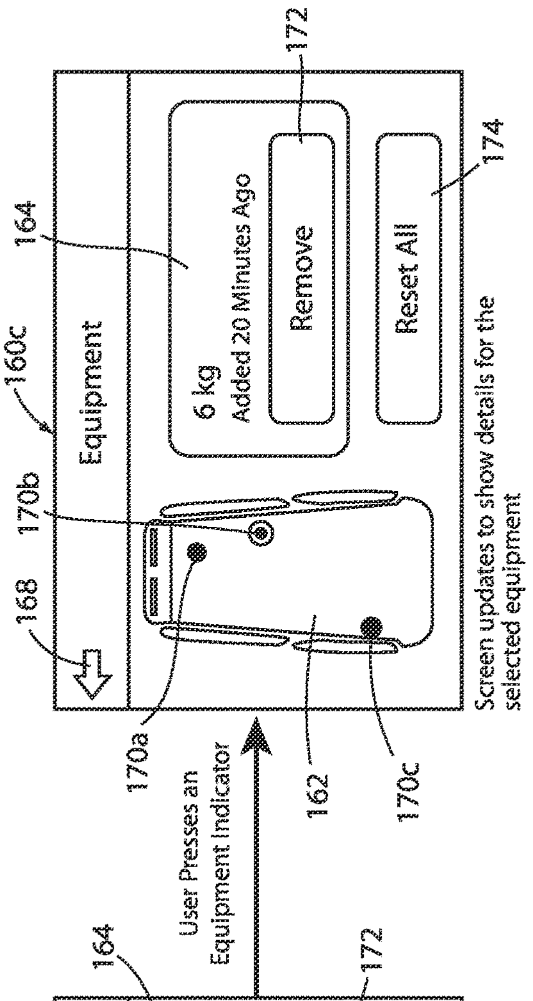
FIG. 11 is a fourth example of the weight log screen illustrating a situation where additional information regarding one of the added objects is being displayed.

FIG. 11 illustrates a weight log screen 160*c* that is displayed by controller 70 when the user has pressed on the object icon 170*b*. That is, as noted earlier, when a caregiver presses on one of the object icons 170, controller 70 is configured to display additional information about the object 90 corresponding to that particular object icon 170. In the example of FIG. 11, the user has pressed on object icon 170*b* and controller 70 is displaying information in message area 164 about the object 90 that corresponds to object icon 170*b*. As can be seen in FIG. 11, object icon 170*b* corresponds to an object 90 that weighs six kg and that was added to patient support apparatus 20 twenty minutes ago.

As can be seen from FIGS. 10 and 11, controller 70 is configured to highlight the object icon 170 that the user has selected. This informs the caregiver which one of the multiple icons 170 the information inside message area 164 pertains to. In the particular examples of FIGS. 10 and 11, controller 70 highlights the selected object icon 170 by placing a blue circle around the perimeter of the circle-shaped object icon 170. Thus, object icon 170*a* of FIG. 10 includes a blue circle around its perimeter and message area 164 displays information about the specific object 90 corresponding to object icon 170*a*; and object icon 170*b* of FIG. 11 includes a blue circle around its perimeter and message area 164 display information about the specific object 90 corresponding to object icon 170*b*. It will of course be understood that object icons 170 can be highlighted by controller 70 in different manners.

FIG. 12 illustrates an example of a weight log screen 160*d* that is displayed on display 60 by controller 70 after a user has pressed on the "remove" control 172. As can be seen therein, controller 70 displays a cancel control 176, a continue control 178, and a confirmation message 180. The confirmation message 180 asks the caregiver to confirm that they wish to remove a selected object 90 from the weight log. In the example of FIG. 12, the confirmation message 180 pertains to the object 90 corresponding to the object icon 170*a*. If the user presses the continue control 178, controller 70 moves ahead with removing the object 90 from the weight log in the manner previously described. That is, controller 70 monitors the outputs of force sensors 54 looking for a reduction in weight from a location on patient support apparatus 20 that corresponds to the weight and location stored in the weight log, and issues an error notification if this isn't detected. On the other hand, if the caregiver presses the cancel control 176, controller 70 returns to displaying the previously displayed screen.

If the caregiver presses on the continue control 178 of screen 160*d* (FIG. 12), controller 70 is configured to display a modified weight log screen, such as the weight log screen 160*e* of FIG. 13. This weight log screen 160*e* shows the patient support apparatus icon 162 with the object icon 170*a* removed therefrom. Object icon 170*a* has been removed because the object 90 corresponding to object icon 170*a* was removed from patient support apparatus 20. In such situations, controller 70 automatically selects one of the remaining object icons 170*b* or 170*c* and displays in message area 164 information about whichever one of the remaining objects it selects.

If the caregiver presses on the reset all or remove all control 174 in any of the various weight log screens 160 shown herein, controller 70 is configured to display a weight log screen 160*f* of the type shown in FIG. 14. Weight log screen 160*f* includes a message displayed in message area 164 asking the caregiver to confirm that they wish to remove or reset all of the objects contained within the weight log. Weight log screen 160*f* further includes the cancel control 176 and the continue control 178. If the user presses the cancel control 176, controller 70 returns to displaying the previously displayed screen without removing any objects from the weight log. If the user presses the continue control 178, controller 70 proceeds to display a screen such as that shown in FIG. 15.

FIG. 15 displays a weight log screen 160*g* in which all objects 90 have been removed from the weight log. When transitioning from screen 160*f* to screen 160*g*, controller 70 is configured to first verify that the caregiver has actually removed all of the objects 90 from the patient support apparatus 20 prior to displaying screen 160*g*. If one or more of the objects 90 are not removed, controller 70 is configured to display an error message.

Figure 16:
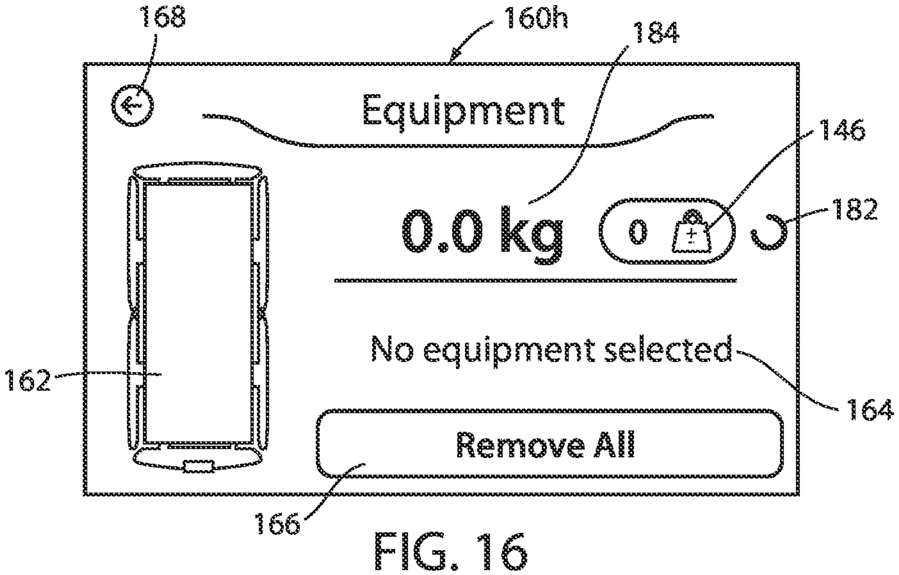
FIG. 16 is a ninth example of the weight log screen that may be displayed during an interim period when the scale system is detecting the addition or removal of an object.

In some embodiments, controller 70 is configured to display an interim weight log screen, such as the interim weight log screen 160*h* shown in FIG. 16. When so configured, controller 70 displays screen 160*h* during the interim between when the time when an object is initially added or removed and the time when the object's addition or removal is confirmed. That is, controller 70 may take a few seconds or more to wait for the weight readings from force sensors 54 to stabilize before concluding that an object has been added or removed from patient support apparatus 20. During this interim period while controller 70 is waiting for the force readings to stabilize, controller 70 may display screen 160*h*.

Screen 160*h* (FIG. 16) includes the patient support apparatus icon 162, the remove all control 166 (which may or may not be functional, depending upon whether there are any objects on the patient support apparatus 20 or not), message area 164, back control 168, weight log icon 146, a spinning icon 182, and an object weight indicator 184. Controller 70 animates spinning icon 182 so that it appears to be spinning in a circle during the interim period between the caregiver adding/removing an object 90 and the stabilization of the weight change caused by the object 90's addition or removal. The spinning icon 182 provides a visual indication to the user that controller 70 is actively performing the weight log update and that the user should wait. This lets the caregiver know that the scale system is actively working, rather than being non-responsive.

Controller 70 also displays the object weight indicator 184 to indicate the weight of the object 90 that is being added or removed. In the example shown in FIG. 16, controller 70 has not yet determined the weight of the object being added/removed, and so shows a 0.0 kg reading at the object weight indicator 184. Once the weight is known, controller 70 displays the weight of object 90 at the object weight indicator 184. In some embodiments, controller 70 is configured to display interim control screen 160*h* for a few moments after the weight has stabilized, and thereafter switch to displaying one of the previously discussed weight log screens 160.

In some embodiments, controller 70 is configured to display a weight log screen of the type shown in FIG. 17 when controller 70 concludes that the location of an added object 90 cannot accurately be determined. FIG. 17 shows a weight log screen 160*i* that controller 70 may be configured to display on display 60 when controller 70 executes step 134 of algorithm 100. As was noted above in the discussion of algorithm 100, controller 70 executes step 132 by determining if the weight of an added object 90 is capable of solely causing the measured change in the center of gravity (as opposed to being partially caused by patient movement), and if it is not, by moving to step 134 where it issues a notification to the user. Weight log screen 160*i* therefore provides a notification to the user that the location of the added object 90 may be in error. Weight log screen 160*i* may also be displayed when other errors are encountered or detected by controller 70 when attempting to compute the location of the object 90.

Weight log screen 160*i* includes an error message 186, a save position control 188, and an uncertainty icon 190. The error message 186 display a message to the caregiver indicating that the location of the added object 90 cannot be determined. In the example shown in FIG. 17, the message states "item position may not be correct." If the user presses the cancel icon 176, controller 70 does not add the object to the weight log. If the user presses the save position control 188, controller 70 saves the calculated positon of the object 90 in the weight log, despite the potential uncertainty of this calculated positon. The save position control 188 therefore acts as a sort of confirmation control in which the caregiver is able to manually confirm that the calculated position of the object 90 is actually correct. The uncertainty icon 190 indicates to the user that the calculated location of object 90 may be uncertain.

Although weight log screen 160*i* is shown as applying to the addition of an object 90, it will be understood that a similar weight log screen may be displayed when an object 90 is removed from patient support apparatus 20 and the location of that removed object doesn't match the location of any objects 90 stored in the weight log. In such a situation, controller 70 may display uncertainty icon 190 on patient support apparatus icon 162 at the location of the nearest object 90 and ask the caregiver to confirm that that object 90 is the one that was removed.

Figure 18:
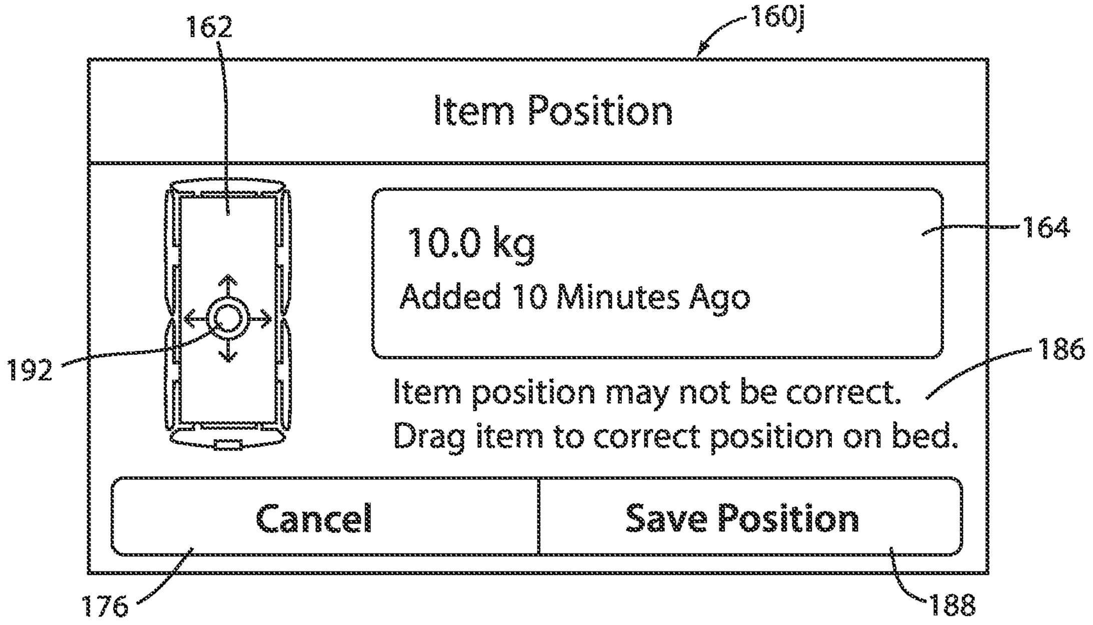
FIG. 18 is an eleventh example of the weight log screen that may be displayed to allow a user to graphically select a location of an object that was added to the patient support apparatus.

In some embodiments, controller 70 is configured to display an alternative weight log screen, such as the weight log screen 160*j* shown in FIG. 18, when the position of an added object has a threshold amount of uncertainty. That is, in some embodiments, controller 70 may be configured to display weight log screen 160*j* on display 60 when controller 70 executes step 134 of algorithm 100. As previously discussed, controller 70 executes step 132 by determining if the weight of an added object 90 is capable of solely causing the measured change in the center of gravity (as opposed to being partially caused by patient movement), and if it is not, by moving to step 134 where it issues a notification to the user. Weight log screen 160*j* therefore provides a notification to the user that the location of the added object 90 may be in error. Weight log screen 160*j* may also be displayed when other errors are encountered or detected by controller 70 when attempting to compute the location of the object 90.

Weight log screen 160*j* (FIG. 18) differs from weight log screen 160*i* (FIG. 17) in that it includes a movable object location icon 192 positioned on patient support apparatus icon 162. Controller 70 is configured to display weight log screen 160*i* when display 60 is a touch screen display, and to allow a user to drag object location icon 192 to different locations on patient support apparatus icon 162. This feature is described in the message 186, which instructs the user to "drag item to correct position on bed." That is, the user looks at the actual location of the item that was added to patient support apparatus 20 and slides icon 192 to a location on patient support apparatus icon 162 that corresponds to the actual location of the item vis-a-vis the actual patient support apparatus 20.

After dragging or sliding icon 192 to the correct location, the user can select the "save position" option 188. When the user selects the save position option 188, controller 70 uses the location of the icon 192 relative to the patient support apparatus icon 162 to set the position of the actual item on patient support apparatus 20. Thus, for example, if the object location icon 192 is slid to a location that corresponds to an X,Y location on patient support apparatus icon 162, controller 70 concludes that the actual item was placed at a corresponding X,Y location on the actual patient support apparatus 20. Controller 70 then uses that actual X,Y location of the object to subtract out the impact to the added item's weight from the calculation of the patient's center of gravity.

For example, if a ten pound object is added to the patient support apparatus 20 at location X, Y, controller 70 may be configured to determine how much of that ten pounds is exerted against each of the four load cells 54 on patient support apparatus 20. These weights may then be subtracted from each load cell reading prior to calculating the patient's center of gravity (in those situations where the ten pound object was added). The center of gravity calculation is subsequently made based on readings from the load cells that have had the weight components of the object removed therefrom, thereby yielding a true calculation of the patient's center of gravity.

In some embodiments, screen 160*j* is displayed instead of screen 160*i*. Alternatively, controller 70 may be configured to display screen 160*j* subsequently to screen 160*i*. In such alternative embodiments, screen 160*i* may be modified to include an option, such as an "adjust location" option that the user can select to cause controller 70 to display screen 160*j*. Other manners for triggering the display of screen 160*j* may also, or alternatively, be implemented.

In some embodiments, controller 70 may be configured to display screen 160*j* automatically in response to a user adding an object, regardless of whether or not controller 70 determines any uncertainty in the position of the object. In such embodiments, the display of object location icon 192 serves as a visual check for the user to either confirm, or not confirm, that controller 70 has correctly determined the location of the added object. If the location of the object location icon 192 matches the actual location of the object 90, he or she can select the "save position" control 188. If the location of the object location icon 192 does not match the actual location of the object 90, he or she can drag object location icon 192 to the correct location vis-a-vis patient support apparatus icon 162 and then select the "save position" control 188. Thus, object location icon 192 provides visual feedback to the user regarding the accuracy of the location of the actual object 90 on patient support apparatus 20.

It will be understood that the content and layout of the various weight log screens 160, 160*a-j* discussed herein can be modified in a variety of different ways in different embodiments of patient support apparatus 20. It will also be understood that the manner of manually navigating to these screens and/or the triggers that cause controller 70 to automatically display these various screens may also vary widely. As was noted, in some embodiments, one or more of the screens 160 are displayed automatically in response to the detection an added or removed object 90, and/or in response to a user pressing on the weight log icon 146 (which may be displayed on one or more screens that are not related to the weight logging function, and which thereby enable the user to quickly navigate to the weight log functionality and screens 160). Still other manners and/or triggers for displaying screens 160 may be implemented.

In some embodiments, controller 70 of patient support apparatus 20 is configured to automatically take one or more actions in response to detecting the addition and/or removal of an object 90 form the litter frame 28 of patient support apparatus 20. For example, in at least one embodiment, controller 70 is configured to attempt to establish wireless communication with the object 90, or its associated tag 92, using object transceiver 74 (FIG. 5). In such embodiments, controller 70 instructs object transceiver 74 to send out a message to the object 90 or tag 92 requesting that the object 90 or tag 92 respond to the message. The message may request that the object 90 or tag 92 respond with information enabling controller 70 to identify the object 90 or tag 92. In some embodiments, the responsive message includes a device identifier and controller 70 includes a list of device identifiers that it consults to determine the identity of the object 90 and/or its tag 92. In other embodiments, controller 70 may be configured to forward the device identifier to server 82 via network transceiver 68 and request that server 82 identify the object.

Regardless of whether controller 70 or patient support apparatus server 82 identifies the object 90 or tag 92, controller 70 may be configured to display the identity of the device on display 60. In some embodiments, controller 70 changes the object icons 170 so that each type of device includes its own type of icon. Additionally, or alternatively, controller 70 may display an identification of the device adjacent to the icon 170 and/or elsewhere on any of the weight log screens 160. Controller 70 may also be configured to forward the identity of the object 90 or tag 92 to patient support apparatus server 82, which then forwards that information to one or more electronic devices 86 that are in communication with server 82. The electronic devices 86, as noted previously, may be in communication with and/or executing a caregiver assistance application 84 that is configured to display information similar to what is shown on any of the weight log screens 160 shown herein. That is, the caregiver assistance application 84 may display a patient support apparatus icon 162 with object icons 170 shown thereon at the locations that correspond to the actual locations of the object(s) 90. If the user presses on any of these icons 170, the caregiver assistance application 84 may be configured to display additional information about the object, such as the weight of the object, the time it was added, etc. This information is displayed on the display(s) 88 of the mobile electronic device(s) 86.

In some embodiments, controller 70 is also configured to automatically take a photo with camera 72 when an object is added to, or removed from, litter frame 28 (as detected automatically through the repetitive monitoring of the outputs of force sensors 54 and the execution of algorithm 100). As was noted, camera 72 is aimed so that its field of view will encompass those locations of patient support apparatus 20 on which objects 90 may be placed that will cause their weight to be detected by force sensors 54. In general, this field of view encompasses the top surface of the mattress positioned on support deck 30, although it will be understood that it may encompass additional viewing areas as well.

In some embodiments, controller 70 is configured to display the photo captured by camera 72 on display 60. This photo may be displayed on any of the weight log screens 160 and, in some embodiments, may be time stamped and saved as part of the weight log. Alternatively, or additionally, controller 70 may forward the captured photo to server 82 for time stamping and/or saving. Server 82 may also or alternatively be configured to share the photo with one or more mobile electronic devices 86 that are assigned to the caregiver(s) associated with the patient who is assigned to that particular patient support apparatus 20. In such embodiments, the mobile electronic devices 86 are configured to display the photo on their respective displays 88. A remotely positioned caregiver can therefore visually see what object has been placed on patient support apparatus 20 by looking at display 88 of his or her electronic device 86.

If controller 70 detects that an object 90 was removed from patient support apparatus 20, controller 70 may be configured to send both a photo taken before the object was removed and a photo taken after the object was removed. These two photos may be shared with server 82, which in turn may utilize caregiver assistance application 84 to share these photos with the appropriate mobile electronic devices 86. Remotely positioned caregivers can therefore see what object 90 has been removed from patient support apparatus 20 by comparing the "before" photo with the "after" photo and seeing which object 90 that appears in the "before" photo is missing from the "after" photo.

In another alternative embodiment, camera 72 may be a video camera that continuously captures images of patient support apparatus 20. In such embodiments, controller 70 may be configured to automatically mark a segment of the video captured by camera 72 in response to the detection of an added or removed object 90. The segment of the video that is marked by controller 70 generally extends from a moment just prior to the object 90 being added or removed to a moment just after the object was added or removed. As with the photos mentioned above, this marked segment of video may then be forwarded to server 82, which in turn may forward it to one or more mobile electronic devices 86, thereby enabling remotely positioned caregivers to see a segment of video in which the object 90 was added or removed.

In some embodiments, controller 70 is configured to decide whether to send a photo or video segment of an added or removed object to server 82 based on an ID received from the object 90 or its tag 92. The ID may be received via object transceiver 74, as discussed above. In such embodiments, for some types of objects 90 or tags 92, controller 70 is configured to not send a photo or video segment to server 82, while for other types of objects 90 or tags 92, controller 70 is configured to forward a photo or video segment to server 82 of these objects 90 being added or removed.

Controller 70, in some embodiments, is configured to analyze the images (whether still photos or video images) captured by camera 72 and to identify the object 90 through visual analysis. This visual analysis may be performed in addition to, or in lieu of, any messages sent by transceiver 74 to object 90 or tag 92 requesting identification from the object 90 or tag 92. In alternative embodiments, the visual analysis of the object 90 may be carried out by server 82, either alone or in combination with controller 70. Regardless of where the visual analysis of the images captured by camera 72 is performed, the visual analysis may be performed in any of the manners disclosed in the following commonly assigned references: U.S. patent 10,121,70 issued to Richard A. Derenne et al. on Nov. 6, 2018, and entitled VIDEO MONITORING SYSTEM; U.S. Pat. No. 10,904,492 issued to Richard Derenne et al. on Jan. 26, 2021, and entitled VIDEO MONITORING SYSTEM; and U.S. patent application Ser. No. 63/218,53 filed Jul. 2, 2021, by inventors Krishna Bhimavarapu et al. and entitled PATIENT VIDEO MONITORING SYSTEM, the complete disclosures of all of which are incorporated herein by reference. It will also be understood that the placement and/or construction of camera(s) 72 may be the same as any of the cameras disclosed in these patent references. Still further, patient support apparatus 20 and/or server 82 may be configured to perform any one or more of the same functions as, or implement the same features as, any of the patient support apparatuses and patient support apparatus servers disclosed in the aforementioned three patent references.

In some embodiments, patient support apparatus 20 includes more than one camera 72 and controller 70 is configured to capture images from each of the multiple cameras 72, and/or to mark segments from the videos of each of the multiple cameras 72, in response to detecting the addition or removal of an object. In such embodiments, controller 70 may be configured to forward multiple images, or multiple video segments, to server 82 for distribution to one or more electronic devices 86.

In some embodiments, one or more depth sensors are included with, or operate in conjunction with, the one or more cameras 72. The depth sensors are adapted to gather depth information about the items that appear within the camera's field of view. Generally speaking the depth sensors detect the distance between the camera and the items that are positioned within the camera's field of view. Further information regarding examples of the types of depth sensors, as well further details regarding their operation, may be found in the following commonly assigned patent references: U.S. Pat. Nos. 10,121,70; 10,904,492; and U.S. patent application Ser. No. 63/218,53; the complete disclosures of which have already been incorporated herein by reference.

Utilizing the depth sensor information, controller 70 is adapted, in some embodiments, to calculate a first position estimate of each of the objects 90 that are added to patient support apparatus 20. In making this calculation, controller 70 utilizes information stored in memory 76 that indicates the location of each camera 72 onboard patient support apparatus 20. Further, the location of each camera 72 onboard patient support apparatus 20 is defined in a manner that is correlated to the known position of the force sensors 54. That is, in some embodiments, memory 76 stores the position of the camera(s) 72 and the force sensors 54 in a common frame of reference, or in some other manner that enables controller 70 to determine the spatial relationship of force sensors 54 to the camera(s) 72.

In those embodiments of patient support apparatus 20 in which controller 70 uses the depth information and visual information from camera(s) 72 to calculate a first position estimate of the object 90, controller 70 may further be configured to independently calculate a second estimate of the location of the added object 90 using the outputs of the force sensors 54 in the manner previously described (i.e. by calculating the center of gravity of the added object 90). In such embodiments, controller 70 may be further adapted to compare the first and second position estimates with each other to determine how much (if any) they differ by. If they differ by more than a threshold, controller 70 may be configured to issue a notification of the type discussed above with respect to step 134 of algorithm 100 (FIG. 6). Indeed, in some embodiments, algorithm 100 is modified to include one or more additional steps that are undertaken with respect to camera(s) 72 and/or object transceiver 74. One example of such a modification is the use of location information gathered from the visual analysis of the images from camera 72 to confirm that an object has been added or removed from a particular location onboard patient support apparatus 20. As noted, this visual analysis of the location of the added or removed object 90 may be carried out in addition to the location calculation process that utilized the force sensors 54.

In some embodiments, controller 70 may be configured to obscure the patient's facial features and/or other features of the patient in the images it captures. In some such embodiments, controller 70 may utilize any of the rendering or other anonymizing functions disclosed in the commonly assigned U.S. patent application 63/218,053, the complete disclosure of which has already been incorporated herein by reference. In other embodiments, controller 70 may utilize other techniques for obscuring the identity of the patient in any of the images captured by camera(s) 72.

It will be understood that, although caregiver assistance application 84 is shown in FIG. 5 to be executed solely by server 82, this may be modified so that caregiver assistance application 84 is executed, either partially or wholly, on one or more of the mobile devices 86 as a mobile app that is downloaded to these devices 86. Similarly, caregiver assistance application 84 may be implemented as an app that executes on server 82 in conjunction with another specialized app that is downloaded to each of the mobile electronic devices 86. Still other variations of caregiver assistance application 84 are possible.

In some embodiments, server 82 may be part of an asset tracking system that monitors the location of the one or more objects 90 that are added to a patient support apparatus 20. In such embodiments, controller 70 and/or server 82 may be configured to forward to an asset tracking system the identification and/or location of any objects 90 that are detected onboard a patient support apparatus 20. In some such embodiments, this location and/or identification information is forwarded to an asset tracking system of the type disclosed in commonly assigned PCT patent application PCT/US2017/041681 (WO 2018/013666) filed Jul. 12, 2017, by inventors David Becker et al. and entitled EQUIPMENT MANAGEMENT SYSTEM, the complete disclosure of which is incorporated herein by reference.

In some embodiments, the teachings disclosed herein may be applied to a piece of furniture, such as a sofa, couch, or the like. When so applied, a plurality of force sensors keep track of the addition of objects to the piece of furniture and a user interface issues a notification to the user when an object is detected or removed. Further, the user interface may provide the user with a display indicating which objects have been detected onboard the piece of furniture, including their weight and dates. In this manner, if a user loses a set of keys, cell phone, or other object in the sofa, couch, or other piece of furniture, the scale system onboard the piece of furniture can indicate to the user that an added weight is currently being detected, thereby prompting the user to search more thoroughly through the piece of furniture.

It will also be understood that controller 70 may be configured to also monitor the outputs of force sensors 54 for implementing a patient exit detection system that may be armed and disarmed by a caregiver. When armed, the exit detection system is configured to issue an alert when the patient exits patient support apparatus 20, or moves beyond one or more boundaries. In some such embodiments, controller 70 calculates the center of gravity of the patient separately from the center of gravity of the objects 90, and issues the exit alert if the patient's center of gravity moves outside of a selected boundary. In such embodiments, controller 70 may be configured to assume that each object 90 remains stationary, or substantially stationary, while positioned on patient support apparatus 20. In some embodiments, the exit detection functions may be carried out in any off the manners disclosed in the following commonly assigned U.S. patent applications: Ser. No. 62/889,254 filed Aug. 20, 2019, by inventors Sujay Sukumaran et al. and entitled PERSON SUPPORT APPARATUS WITH ADJUSTABLE EXIT DETECTION ZONES, and/or Ser. No. 15/266,575 filed Sep. 15, 2016, by inventors Anuj K. Sidhu et al. and entitled PERSON SUPPORT APPARATUSES WITH EXIT DETECTION SYSTEMS, the complete disclosures of both of which are incorporated herein by reference.

It will also be understood that controller 70 may be configured to adjust the outputs of force sensors 54 to take into account the tilting of litter frame 28. That is, in some embodiments, force sensors 54 are load sensors whose outputs do not reflect the true load placed thereon when the load applied to the load cell is tilted, such as may happen when litter frame 28 is tilted out of a horizontal orientation. In such cases, the level of tilt is detected by one or more sensors onboard patient support apparatus 20 and a simple trigonometric calculation (based on the detected tilt angle) is applied to the outputs of the load cells 54 by controller 70 to remove this error in the load measurement. These tilt-adjusted load cell readings are then processed and used to compute the center of the gravity and/or weights of the patients and/or objects 90.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:

a support surface adapted to support a patient thereon;

a plurality of force sensors adapted to detect downward forces exerted on the support surface;

a display;

a transceiver; and a controller adapted to analyze outputs from the plurality of force sensors to determine if a load added to the support surface corresponds to a patient or an object, the controller further adapted to perform the following:

if the load corresponds to an object, to send a message wirelessly via the transceiver to the object to attempt to establish communication with at least one of the object or an electronic tag coupled to the object, to automatically determine a location of the object on the patient support apparatus and display the location of the object on the display; and if the load corresponds to the patient, to not automatically determine a location of the patient on the patient support apparatus and to not display a location of the patient on the display.

2. The patient support apparatus of claim 1 wherein, if the load corresponds to a patient, the controller is adapted to not send the message via the transceiver.

3. The patient support apparatus of claim 1 wherein the controller is further adapted to determine if the load added to the support surface corresponds to a patient or an object by comparing a magnitude of the load to a threshold, and if the load is greater than the threshold, concluding the load corresponds to a patient, and if the load is less than the threshold, concluding the load corresponds to an object.

4. The patient support apparatus of claim 1 wherein the display is a touchscreen, and the controller is further adapted to display a patient support apparatus icon and an object icon on the display, and wherein the controller is still further adapted to display additional information about the object in response to a user pressing on the object icon.

5. The patient support apparatus of claim 4 wherein the additional information includes at least one of the following: a weight of the object, a time when the object was added to the patient support apparatus, a day when the object was added to the patient support apparatus, a coordinate location of the object, or an identification of the object.

6. The patient support apparatus of claim 1 further comprising a camera having a field of view aimed to encompass the support surface, and wherein the controller is further adapted to instruct the camera to capture an image of the object after the object has been added to the support surface.

7. The patient support apparatus of claim 1 wherein the message is sent to the electronic tag coupled to the object.

8. The patient support apparatus of claim 7 wherein the message is adapted to prompt the electronic tag to respond to the message.

9. The patient support apparatus of claim 7 wherein the message is adapted to prompt the electronic tag to respond with identification information identifying the object.

10. The patient support apparatus of claim 1 further comprising a camera having a field of view aimed to encompass the support surface, and wherein if the load corresponds to an object, the controller is adapted to instruct the camera to capture an image of the object after the object has been added to the support surface, and the controller is further adapted to analyze the image in order to determine a first location estimate of the object relative to the patient support apparatus.

11. The patient support apparatus of claim 10 wherein the controller is further adapted to analyze outputs from the force sensors to determine a second location estimate of the object.

12. The patient support apparatus of claim 11 wherein the controller is further adapted to compare the first location estimate of the object to the second location estimate of the object.

13. The patient support apparatus of claim 12 wherein the controller is further adapted to issue a notification if the first location estimate differs from the second location estimate by more than a threshold.

14. The patient support apparatus of claim 1 further comprising a touchscreen and wherein, if the load corresponds to an object, the controller is further adapted to perform the following:

display a location selection icon and a patient support apparatus icon on the touchscreen, the location selection icon being movable by a user with respect to the patient support apparatus icon;

determine a location of the location selection icon with respect to the patient support apparatus icon after the user has moved the location selection icon; and use the location of the location selection icon with respect to the patient support apparatus icon as the actual location of the object with respect to the patient support apparatus.

15. The patient support apparatus of claim 1 wherein, if the load corresponds to an object, the controller is further adapted to determine a center of gravity change between a first center of gravity calculation made before the object was added and a second center of gravity calculation made after the object was added, to determine if the center of gravity change can be accounted for solely by the addition of the object to the support surface and, if not, to issue a notification to a user.

16. The patient support apparatus of claim 15 wherein the controller is further adapted to calculate a location of the object if the center of gravity change can be accounted for solely by the addition of the object.

17. The patient support apparatus of claim 16 wherein the controller is configured to determine if the center of gravity change can be accounted for solely by the addition of the object to the support surface by performing the following:

determining a weight of the object;

determining a ratio of the weight of the object to a weight measured prior to the addition of the object to the support surface;

using the ratio to determine a theoretical location where the object would have to be placed to account for the center of gravity change;

determining if the theoretical location is inside or outside of a boundary; and concluding the center of gravity change can be accounted for solely by the addition of the object if the theoretical location is inside of the boundary.

18. The patient support apparatus of claim 17 wherein the boundary corresponds to a perimeter of the support surface.

19. The patient support apparatus of claim 18 wherein the controller is configured to conclude that the center of gravity change cannot be accounted for solely by the addition of the object if the theoretical location is outside of the boundary.

* * * * *